US010393751B2

(12) United States Patent
Albert et al.

(10) Patent No.: US 10,393,751 B2
(45) Date of Patent: Aug. 27, 2019

(54) SPECIFIC PEPTIDE BINDERS TO PROTEINS IDENTIFIED VIA SYSTEMATIC DISCOVERY, MATURATION AND EXTENSION PROCESS

(71) Applicant: Roche Sequencing Solutions, Inc., Pleasanton, CA (US)

(72) Inventors: Thomas Albert, Verona, WI (US); Ryan Bannen, Madison, WI (US); Victor Lyamichev, Madison, WI (US); Jigar Patel, Madison, WI (US); Eric Sullivan, Madison, WI (US)

(73) Assignee: ROCHE SEQUENCING SOLUTIONS, INC., Pleasanton, CA (US)

( * ) Notice: Subject to any disclaimer, the term of this patent is extended or adjusted under 35 U.S.C. 154(b) by 0 days.

(21) Appl. No.: 15/132,951

(22) Filed: Apr. 19, 2016

(65) Prior Publication Data

US 2016/0305952 A1 Oct. 20, 2016

Related U.S. Application Data

(60) Provisional application No. 62/150,202, filed on Apr. 20, 2015.

(51) Int. Cl.
*C07K 7/06* (2006.01)
*C07K 7/08* (2006.01)
*G01N 33/68* (2006.01)

(52) U.S. Cl.
CPC ........... *G01N 33/6845* (2013.01); *C07K 7/06* (2013.01); *C07K 7/08* (2013.01); *G01N 2333/36* (2013.01); *G01N 2333/525* (2013.01); *G01N 2333/96455* (2013.01); *G01N 2333/972* (2013.01); *G01N 2333/974* (2013.01)

(58) Field of Classification Search
CPC .................................................. G01N 33/6845
USPC ............................................................ 506/9
See application file for complete search history.

(56) References Cited

U.S. PATENT DOCUMENTS

| | | | |
|---|---|---|---|
| 5,143,854 A | 9/1992 | Pirrung et al. | |
| 5,571,639 A | 11/1996 | Hubbell et al. | |
| 5,593,839 A | 1/1997 | Hubbell et al. | |
| 5,965,698 A | 10/1999 | Evans et al. | |
| 6,620,584 B1 | 9/2003 | Chee et al. | |
| 7,867,755 B2 | 1/2011 | Joos | |
| 8,076,452 B2 | 12/2011 | Erdmann | |
| 8,244,484 B2 | 8/2012 | Lee et al. | |
| 8,969,255 B2 | 3/2015 | Johnston et al. | |
| 2005/0255491 A1 | 11/2005 | Lee et al. | |
| 2010/0022448 A1 | 1/2010 | New | |
| 2010/0160177 A1* | 6/2010 | Merbl | G01N 33/57484 506/9 |
| 2014/0349888 A1 | 11/2014 | Rajasekaran et al. | |
| 2015/0185216 A1 | 7/2015 | Albert et al. | |

FOREIGN PATENT DOCUMENTS

| | | | |
|---|---|---|---|
| EP | 0728520 A1 | 8/1996 | |
| EP | 1914550 A1 | 4/2008 | |
| JP | 2008141995 A | 6/2008 | |
| WO | 19900015070 A1 | 12/1990 | |
| WO | 19930006121 A1 | 4/1993 | |
| WO | 19930009668 A1 | 5/1993 | |
| WO | 19930018054 A2 | 9/1993 | |
| WO | 19950012608 A1 | 5/1995 | |
| WO | 19950035503 A1 | 12/1995 | |
| WO | 19960003649 A1 | 2/1996 | |
| WO | 19970022617 A1 | 6/1997 | |
| WO | 20010092523 A2 | 12/2001 | |
| WO | WO 0192523 A2 * | 12/2001 | ............. C07K 14/47 |
| WO | 20020031510 A1 | 4/2002 | |
| WO | 20030029288 A2 | 4/2003 | |
| WO | 20040001064 A2 | 12/2003 | |
| WO | 2004111636 A2 | 12/2004 | |
| WO | 20050025497 A2 | 3/2005 | |
| WO | 20050088310 A2 | 9/2005 | |
| WO | 20100052939 A1 | 5/2010 | |
| WO | 20130119845 A1 | 8/2013 | |
| WO | 20150970T7 A2 | 7/2015 | |
| WO | 19910018980 A1 | 12/2017 | |

OTHER PUBLICATIONS

Livnah et al., PNAS, USA, vol. 90, pp. 5076-5080, Jun. 1993 (Year: 1993).*
Brochure, Peptide Libraries, GenScript: The Biology of CRO.
Hansen, Lajla Bruntse et al.,, Identification and Mapping of Linear Antibody Epitopes in Human Serum Albumin Using High Density Peptied Arrays, Jul. 2013, e68902 pp. 1-10, 8(7).
Hilpert, K. et al.,, Anti-c-myc antibody 9E10: epitope key positions and variability characterized using peptied spot synthesis on cellulose, 2001, pp. 803-806, 14(10).
International Search Report, PCT/EP2014/078658, dated Mar. 17, 2015.
Lowman, H.B., Bacteriophage Display and Discovery of Peptide Leads for Drug Development, Annu. Rev. Biophys. Biomol. Struct., (1997), pp. 401-424, vol. 26.
Raffler, Nikolai A. et al.,, A Novel Class of Small Functional Peptides that Bind and Inhibit Human-Thrombin Isolated by mRNA Display, Chemistry & Biology, Jan. 2003, pp. 69-79, 10.
Reineke, Ulrich et al.,, Identification of distinct antibody epitopes and mimotopes from a peptide array of 5520 randomly generated sequences, Journal of Immunological Methods, 2002, pp. 37-51, 267.
Rickles, Richard J., et al., Phage display selection of ligand residues important for Src homology 3 domain binding specificity, Biochemistry, Nov. 1995, pp. 10909-10913, 92.

(Continued)

*Primary Examiner* — Karla A Dines
(74) *Attorney, Agent, or Firm* — Daniel Agnew; Eric Grant Lee

(57) ABSTRACT

The invention provides novel peptide binders for streptavidin (SA), Taq polymerase and several human proteins: Prostate Specific Antigen (PSA), thrombin, Tumor Necrosis Factor Alpha (TNFα), and Urokinase-type Plasminogen Activator (uPA).

20 Claims, 4 Drawing Sheets

Specification includes a Sequence Listing.

(56) References Cited

OTHER PUBLICATIONS

Schmidt, Thomas G.M. and Skerra, Arne, The random peptide library-assisted engineering of a C-terminal affinity peptide, useful for the detection and purification of a functional Ig Fv fragment, Protein Engineering, Jan. 1993, pp. 109-122, 1.
Shin, Dong-Sik, et al., Combinatorial Solid Phase Peptide Synthesis and Bioassays, Journal of Biochemistry and Molecular Biology, Sep. 2005, pp. 517-525, 38(5).
Teixeira, A., et al., The Use of DODT as a Non-Malodorous Scavenger in FMOC-Based Peptide Synthesis, Protein and Peptide Letters, (2002), pp. 379-385, vol. 9.
White, Andrew D., et al., Standardizing and Simplifying Analysis of Peptide Library Data, Journal of Chemical Information and Modeling, 2013, pp. 493-499, 53.
Wilson, David S., et al., The use of mRNA display to select high-affinity protein-binding peptides, PNAS, Mar. 27, 2001, pp. 3750-3755, 98(7).
Lyamichevn et al., "Stepwise Evolution Improves Identification of Diverse Peptides Binding to a Protein Target", scientific reports, Sep. 21, 2017;7(1):12116. doi: 10.1038/s41598-017-12440-1.
Skerra, A et al, Use of the Strep-Tag and Streptavidin for Detection and Purification of Recombinant Proteins, Meth Enzym, (2000), pp. 271-304, vol. 326.

\* cited by examiner

SEQUENCE LISTING

```
<160> NUMBER OF SEQ ID NOS: 243

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 1

Leu Gly Glu Tyr His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 2

Phe Asp Glu Trp Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 3

Pro Ala Trp Ala His
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 4

Asp Pro Phe Gly Trp
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 5

Arg Pro Gly Trp Lys
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 6

Asp Tyr Leu Gly Glu Tyr His Gly Gly
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 7

Asn Ser Phe Asp Glu Trp Leu Asn Gln
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 8

Asn Ser Phe Asp Glu Trp Leu Gln Lys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 9

Asn Ser Phe Asp Glu Trp Leu Ala Asn
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 10

Pro Ala Pro Ala Trp Ala His Gly Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 11

Arg Ala Pro Ala Trp Ala His Gly Gly
1               5
```

```
<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 12

Ser Gly Asp Pro Phe Gly Trp Ser Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 13

Arg Pro Gly Trp Lys Leu Trp
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 14

His Glu Phe Ser Phe
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 15

Gln Gln His Glu Phe Ser Phe Ala Gln
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 16

Gly Gln His Glu Phe Ser Phe Gly Thr
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 17

Phe Gln Gln His Glu Phe Ser Phe Ala Gln Gln
1               5                   10

<210> SEQ ID NO 18
```

<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 18

Gly Gln His Glu Phe Ser Phe Gly Pro Ala Ile
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 19

His Tyr Phe Glu Phe
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 20

Gly Glu His Tyr Phe Glu Phe Gln Gln
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 21

Gly Glu His Tyr Phe Glu Phe Ala Pro
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 22

Gln Gln His Tyr Phe Glu Phe Glu Lys
1               5

<210> SEQ ID NO 23
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 23

Ala Gln Gly His Tyr Phe Glu Phe Glu Lys Gln
1               5                   10

<210> SEQ ID NO 24
<211> LENGTH: 11

```
<212> TYPE: PRT
<213> ORGANISM: Artificial Sequence
<220> FEATURE:
<223> OTHER INFORMATION: Synthetic Peptide Sequence

<400> SEQUENCE: 24

Gln Gly Glu His Tyr Phe Thr Phe Gln Gln Pro
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 25

Gly Glu His Tyr Phe Thr Phe Glu Pro Ala Gly
1               5                   10

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 26

Trp Lys Ala Glu Lys
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 27

Phe Gly Trp Lys Ala Glu Lys Phe Asn
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 28

Phe Gly Trp Lys Thr Glu Lys Phe Asn Ser
1               5                   10

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 29

Trp Asp Trp Asp Trp
1               5

<210> SEQ ID NO 30
<211> LENGTH: 9
<212> TYPE: PRT
```

```
<213> ORGANISM: Artificial Sequence
<220> FEATURE:
<223> OTHER INFORMATION: Synthetic Peptide Sequence

<400> SEQUENCE: 30

Arg Ser Trp Asp Trp Asp Trp Lys Lys
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 31

Arg Ser Trp Asp Trp Asp Trp Lys Lys Thr
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 32

Trp Lys Glu Asp Trp
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 33

Tyr Lys Trp Lys Glu Asp Trp Lys Trp
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 34

Phe Gly Lys Trp Lys Glu Asp Asn Lys Trp
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 35

Trp Thr Lys Val Lys
1               5

<210> SEQ ID NO 36
<211> LENGTH: 9
<212> TYPE: PRT
<213> ORGANISM: Artificial Sequence
```

<220> FEATURE:
<223> OTHER INFORMATION: Synthetic Peptide Sequence

<400> SEQUENCE: 36

Tyr Glu Trp Thr Lys Val Lys Asn Tyr
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 37

Tyr Ser Trp Thr Lys Val Lys Asp Tyr
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 38

Tyr Glu Trp Thr Lys Tyr Lys Asn Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 39

Tyr Ser Trp Asn Lys Tyr Lys Asp Tyr
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 40

Phe Glu Val Tyr Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 41

Gly Gln Phe Glu Val Tyr Leu Pro Gly
1               5

<210> SEQ ID NO 42
<211> LENGTH: 9
<212> TYPE: PRT
<213> ORGANISM: Artificial Sequence
<220> FEATURE:

<223> OTHER INFORMATION: Synthetic Peptide Sequence

<400> SEQUENCE: 42

Thr Asp Phe Glu Val Tyr Leu Pro Lys
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 43

Gly Gln Phe Glu Val Tyr Ile Pro Gly Ala
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 44

Thr Asp Phe Glu Val Tyr Phe Pro Lys Thr
1               5                   10

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 45

Trp Thr Val Tyr Ala
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 46

Ser Glu Trp Thr Val Tyr Ala Gly Asn
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 47

Gly Asp Trp Thr Val Tyr Ala Gly Asn
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic Peptide Sequence

```
<400> SEQUENCE: 48

Ala Ser Glu Trp Thr Val Tyr Ala Gly Asn
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 49

Ala Gly Asp Trp Thr Val Tyr Ala Gly Leu Gly
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 50

Ala Leu Asp Trp Gln Val Tyr Ala Gly Phe Gly
1               5                   10

<210> SEQ ID NO 51
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 51

Trp Glu Val His Leu
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 52

Thr Gly Trp Glu Val His Leu Gly Lys
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 53

Gly Thr Gly Trp Glu Val His Leu Gly Lys
1               5                   10

<210> SEQ ID NO 54
<211> LENGTH: 5
<212> TYPE: PRT
<213> ORGANISM: Artificial Sequence
<220> FEATURE:
<223> OTHER INFORMATION: Synthetic Peptide Sequence
```

```
<400> SEQUENCE: 54

Arg Ser Ile Leu Tyr
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 55

Ser Cys Arg Ser Ile Leu Tyr Gly Gln
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 56

Gln Ser Cys Arg Ser Ile Leu Tyr Gly Asp
1               5                   10

<210> SEQ ID NO 57
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 57

Pro Ile Asn Leu Gly
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 58

Trp Ala Pro Ile Asn Leu Gly Gln Arg
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 59

Pro Ala Pro Ile Asn Leu Gly Asn Arg
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 60
```

Val Pro Ile Arg Leu
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 61

Tyr Ala Val Pro Ile Arg Leu Gly Ala
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 62

Trp Pro Ile Asn Leu
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 63

Arg Tyr Trp Pro Ile Asn Leu Gly Lys
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 64

Tyr Arg Trp Pro Ile Asn Leu Gly Lys
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 65

Ala Pro Val Arg Leu
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 66

```
Lys Tyr Ala Pro Val Arg Leu Gly Ser
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 67

Arg Gln Ile Phe Leu
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 68

Asp Gly Arg Gln Ile Phe Leu Gln Lys
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 69

Pro Ile Arg Leu Lys
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 70

Asn Trp Pro Ile Arg Leu Lys Pro Ala
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 71

Tyr Ala Pro Ile Arg Leu Lys Pro Gln
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 72

Pro Val Gly Ser Arg
```

```
<210> SEQ ID NO 73
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 73

Gly Trp Pro Val Gly Ser Arg Gln Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 74

Tyr Gly Pro Val Gly Ser Arg Gly Phe
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 75

Arg Asp Pro Gly Arg
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 76

Glu Asn Arg Asp Pro Gly Arg Ser Phe
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 77

Ala Ile Ala Ile Phe
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 78

Gly Pro Ala Ile Ala Ile Phe Gly Gly
1               5
```

<210> SEQ ID NO 79
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 79

Gln Ala Ala Ile Ala Ile Phe Gly Gly
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 80

Gly Pro Ala Val Ala Ile Phe Gly Gly
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 81

Glu Ala Ala Val Ala Ile Phe Gly Gly
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 82

Gln Ala Ala Val Ala Ile Phe Gly Asp
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 83

Thr Ala Val Phe Val
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 84

Gly Gly Thr Ala Val Phe Val Asn Thr
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 85

Ser Ser Thr Ala Val Phe Val Asn Gln
1               5

<210> SEQ ID NO 86
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 86

Gly Gly Thr Ala Val Phe Val Val Asn Thr
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 87

Asp Ser Thr Ala Val Phe Val Asn Thr
1               5

<210> SEQ ID NO 88
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 88

Ala Leu Tyr Leu Phe
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 89

Asn Gly Ala Leu Tyr Leu Phe Gly Asp
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 90

Gln Gly Ala Leu Tyr Leu Phe Gly Asp
1               5

-continued

```
<210> SEQ ID NO 91
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 91

Val Thr Val Tyr Val
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 92

Thr Ser Val Thr Val Tyr Val Asn Asn
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 93

Gln Ser Val Thr Val Tyr Val Asn Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 94

Thr Ser Val Thr Val Trp Val Asn Asn
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 95

Gln Ser Val Ser Val Tyr Val Asn Thr
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 96

Asn Ala Tyr Phe Ser
1               5

<210> SEQ ID NO 97
```

```
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 97

Tyr Glu Asn Ala Tyr Phe Ser Gly Ser
1               5

<210> SEQ ID NO 98
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 98

Tyr Glu Asn Ala Tyr Phe Ser Gly Ser Gly
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 99

Gln Glu Asn Ala Tyr Phe Ser Gly Asn Gly
1               5                   10

<210> SEQ ID NO 100
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 100

Asn Asp Lys Phe Ser
1               5

<210> SEQ ID NO 101
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 101

Tyr Asn Asp Lys Phe
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 102

Val Gln Asn Asp Lys Phe Ser Gly Ser
1               5

<210> SEQ ID NO 103
<211> LENGTH: 11
```

```
<212> TYPE: PRT
<213> ORGANISM: Artificial Sequence
<220> FEATURE:
<223> OTHER INFORMATION: Synthetic Peptide Sequence

<400> SEQUENCE: 103

Trp Gly Val Gln Asn Asp Lys Phe Ser Gly Ser
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 104

Val Val Trp Asn Asp Lys Phe Ser Gly Asn
1               5                   10

<210> SEQ ID NO 105
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 105

His Glu Thr Ala Arg
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 106

Cys Gly His Glu Thr Ala Arg Asn Trp
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 107

Cys Ala His Glu Thr Ala Arg Asn Trp
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 108

Arg Ser Glu Lys Phe
1               5

<210> SEQ ID NO 109
<211> LENGTH: 9
<212> TYPE: PRT
```

<213> ORGANISM: Artificial Sequence
<220> FEATURE:
<223> OTHER INFORMATION: Synthetic Peptide Sequence

<400> SEQUENCE: 109

Tyr Val Arg Ser Glu Lys Phe Thr Gly
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 110

Thr Ala Arg Ser Glu Lys Phe Thr Gly
1               5

<210> SEQ ID NO 111
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 111

Glu Gly Tyr Gly Arg Ser Glu Lys Phe Thr
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 112

Trp Gly Thr Gly Arg Ser Glu Lys Phe Thr
1               5                   10

<210> SEQ ID NO 113
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 113

Leu Ala Glu Tyr His
1               5

<210> SEQ ID NO 114
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 114

Asn Tyr Pro Asp Trp
1               5

<210> SEQ ID NO 115
<211> LENGTH: 5
<212> TYPE: PRT
<213> ORGANISM: Artificial Sequence

```
<220> FEATURE:
<223> OTHER INFORMATION: Synthetic Peptide Sequence

<400> SEQUENCE: 115

Ser Trp Asp Lys Trp
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 116

Leu Arg Phe Asp Thr
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 117

Asn Ala Trp Ala His
1               5

<210> SEQ ID NO 118
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 118

Trp Arg Gly Trp Leu
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 119

Tyr Gly Pro Tyr Lys
1               5

<210> SEQ ID NO 120
<211> LENGTH: 5
<212> TYPE: PRT
<213> ORGANISM: Artificial Sequence
<220> FEATURE:
<223> OTHER INFORMATION: Synthetic Peptide Sequence

<400> SEQUENCE: 120

Phe Tyr Gly Lys Tyr
1               5

<210> SEQ ID NO 121
<211> LENGTH: 9
<212> TYPE: PRT
<213> ORGANISM: Artificial Sequence
<220> FEATURE:
```

```
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 121

Xaa Xaa Phe Asp Glu Trp Leu Xaa Xaa
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 122

Asp Ser Phe Asp Glu Trp Leu Ala Gly
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 123

Asn Ser Phe Asp Glu Trp Leu Ala Gly
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 124

Asn Ser Phe Asp Glu Trp Leu Asn Gln
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 125

Xaa Xaa Pro Ala Trp Ala His Xaa Xaa
1               5

<210> SEQ ID NO 126
<211> LENGTH: 9
<212> TYPE: PRT
```

```
<213> ORGANISM: Artificial Sequence
<220> FEATURE:
<223> OTHER INFORMATION: Synthetic Peptide Sequence

<400> SEQUENCE: 126

Pro Val Pro Ala Trp Ala His Gly Gly
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 127

Tyr Gly Pro Ala Trp Ala His Gly Gly
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 128

Phe Ala Pro Ala Trp Ala His Gly Gly
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 129

Xaa Xaa Phe Glu Val Tyr Leu Xaa Xaa
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 130

Asn Gly Phe Glu Val Tyr Leu Pro Gly
1               5

<210> SEQ ID NO 131
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 131
```

```
Gly Asn Gly Phe Glu Val Tyr Leu Pro Gly Gly
1               5                   10
```

<210> SEQ ID NO 132
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 132

```
Gly Gly Gln Phe Glu Val Tyr Leu Pro Gly Gly
1               5                   10
```

<210> SEQ ID NO 133
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 133

```
Gly Thr Asp Phe Glu Val Tyr Leu Pro Lys Gly
1               5                   10
```

<210> SEQ ID NO 134
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (2)..(2)
<223> OTHER INFORMATION: X is G or N

<400> SEQUENCE: 134

```
Gly Xaa Gln Phe Glu Val Tyr Ile Pro Gly Ala
1               5                   10
```

<210> SEQ ID NO 135
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 135

```
Gly Thr Asp Phe Glu Val Tyr Phe Pro Lys Ile
1               5                   10
```

<210> SEQ ID NO 136
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 136

```
Xaa Xaa Trp Thr Val Tyr Ala Xaa Xaa
1               5
```

<210> SEQ ID NO 137
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 137

Gly Ser Glu Trp Thr Val Tyr Ala Gly Asn Gly
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 138

Gly Gly Asp Trp Thr Val Tyr Ala Gly Asn Gly
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (11)..(11)
<223> OTHER INFORMATION: X is G or K

<400> SEQUENCE: 139

Ala Ser Glu Trp Thr Val Tyr Ala Gly Asn Xaa
1               5                   10

<210> SEQ ID NO 140
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 140

Xaa Xaa Trp Glu Val His Leu Xaa Xaa
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 141

Gly Gln Trp Glu Val His Leu Gly Lys
1               5

<210> SEQ ID NO 142
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 142

Gly Thr Gly Trp Glu Val His Leu Gly Lys Gly
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 143

Gly Gly Gln Trp Glu Val His Leu Gly Lys Gly
1               5                   10

<210> SEQ ID NO 144
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 144

Xaa Xaa Arg Ser Ile Leu Tyr Xaa Xaa
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 145

Ser Cys Arg Ser Ile Leu Tyr Asn Asp
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 146

Ser Cys Arg Ser Ile Leu Tyr Gly Pro
1               5

<210> SEQ ID NO 147
<211> LENGTH: 11
<212> TYPE: PRT
<213> ORGANISM: Artificial Sequence
<220> FEATURE:
<223> OTHER INFORMATION: Synthetic Peptide Sequence

```
<400> SEQUENCE: 147

Gly Ser Cys Arg Ser Ile Leu Tyr Gly Gln Gly
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 148

Gly Ser Cys Arg Ser Ile Leu Tyr Asn Asp Gly
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 149

Gly Ser Cys Arg Ser Ile Leu Tyr Gly Pro Gly
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 150

Gln Ser Cys Arg Ser Ile Leu Tyr Gly Asp Gly
1               5                   10

<210> SEQ ID NO 151
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 151

Xaa Xaa Pro Ile Asn Leu Gly Xaa Xaa
1               5

<210> SEQ ID NO 152
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 152

Gly Trp Ala Pro Ile Asn Leu Gly Gln Arg Gly
1               5                   10
```

```
<210> SEQ ID NO 153
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 153

Gly Pro Ala Pro Ile Asn Leu Gly Asn Arg Gly
1               5                   10

<210> SEQ ID NO 154
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 154

Xaa Xaa Val Pro Ile Arg Leu Xaa Xaa
1               5

<210> SEQ ID NO 155
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 155

Gly Tyr Ala Val Pro Ile Arg Leu Gly Ala Gly
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 156

Xaa Xaa Trp Pro Ile Asn Leu Xaa Xaa
1               5

<210> SEQ ID NO 157
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 157

Gly Arg Tyr Trp Pro Ile Asn Leu Gly Lys Gly
```

```
1               5                   10
```

<210> SEQ ID NO 158
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 158

```
Gly Tyr Arg Trp Pro Ile Asn Leu Gly Lys Gly
1               5                   10
```

<210> SEQ ID NO 159
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 159

```
Xaa Xaa Ala Pro Val Arg Leu Xaa Xaa
1               5
```

<210> SEQ ID NO 160
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 160

```
Gly Lys Tyr Ala Pro Val Arg Leu Gly Ser Gly
1               5                   10
```

<210> SEQ ID NO 161
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 161

```
Xaa Xaa Arg Gln Ile Phe Leu Xaa Xaa
1               5
```

<210> SEQ ID NO 162
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 162

Gly Asp Gly Arg Gln Ile Phe Leu Gln Lys Gly
1               5                   10

<210> SEQ ID NO 163
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 163

Xaa Xaa Pro Ile Arg Leu Lys Xaa Xaa
1               5

<210> SEQ ID NO 164
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 164

Gly Asn Trp Pro Ile Arg Leu Lys Pro Ala Gly
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 165

Gly Tyr Ala Pro Ile Arg Leu Lys Pro Gln Gly
1               5                   10

<210> SEQ ID NO 166
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 166

Xaa Xaa Pro Val Gly Ser Arg Xaa Xaa
1               5

<210> SEQ ID NO 167
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 167

Gly Gly Trp Pro Val Gly Ser Arg Gln Tyr Gly
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 168

Gly Tyr Gly Pro Val Gly Ser Arg Gly Phe Gly
1               5                   10

<210> SEQ ID NO 169
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 169

Xaa Xaa Arg Asp Pro Gly Arg Xaa Xaa
1               5

<210> SEQ ID NO 170
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 170

Gly Glu Asn Arg Asp Pro Gly Arg Ser Phe Gly
1               5                   10

<210> SEQ ID NO 171
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 171

Xaa Xaa Ala Ile Ala Ile Phe Xaa Xaa
1               5

<210> SEQ ID NO 172
<211> LENGTH: 9
<212> TYPE: PRT
<213> ORGANISM: Artificial Sequence

```
<220> FEATURE:
<223> OTHER INFORMATION: Synthetic Peptide Sequence
<220> FEATURE:
<221> NAME/KEY: MISC_FEATURE
<222> LOCATION: (2)..(2)
<223> OTHER INFORMATION: X is A or S or T
<220> FEATURE:
<221> NAME/KEY: MISC_FEATURE
<222> LOCATION: (9)..(9)
<223> OTHER INFORMATION: X is G or S

<400> SEQUENCE: 172

Glu Xaa Ala Val Ala Ile Phe Gly Xaa
1               5

<210> SEQ ID NO 173
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (2)..(2)
<223> OTHER INFORMATION: X is A or Q

<400> SEQUENCE: 173

Gln Xaa Ala Val Ala Ile Phe Gly Asp
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 174

Xaa Xaa Thr Ala Val Phe Val Xaa Xaa
1               5

<210> SEQ ID NO 175
<211> LENGTH: 10
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (1)..(1)
<223> OTHER INFORMATION: X is G or Q

<400> SEQUENCE: 175

Xaa Gly Thr Ala Val Phe Val Val Asn Thr
1               5                   10

<210> SEQ ID NO 176
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
```

<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 176

Xaa Xaa Ala Leu Tyr Leu Phe Xaa Xaa
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 177

Asp Gly Ala Leu Tyr Leu Phe Gly Asn
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 178

Xaa Xaa Val Thr Val Tyr Val Xaa Xaa
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (4)..(4)
<223> OTHER INFORMATION: X is T or S

<400> SEQUENCE: 179

Thr Ser Val Xaa Val Trp Val Asn Asn
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

```
<400> SEQUENCE: 180

Xaa Xaa His Glu Phe Ser Phe Xaa Xaa
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 181

Tyr Glu His Glu Phe Ser Phe Gly Thr
1               5

<210> SEQ ID NO 182
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 182

Gly Gln Gln His Glu Phe Ser Phe Ala Gln Gly
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 183

Gly Gln His Glu Phe Ser Phe Gly Thr Gly Gly
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 184

Gly Tyr Glu His Glu Phe Ser Phe Gly Thr Gly
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (7)..(7)
<223> OTHER INFORMATION: X is S or T
<220> FEATURE:
<221> NAME/KEY: MISC_FEATURE
<222> LOCATION: (11)..(11)
<223> OTHER INFORMATION: X is Q or P

<400> SEQUENCE: 185

Phe Gln Gln His Glu Phe Xaa Phe Ala Gln Xaa
1               5                   10
```

```
<210> SEQ ID NO 186
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 186

Xaa Xaa His Tyr Phe Glu Phe Xaa Xaa
1               5

<210> SEQ ID NO 187
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 187

Gly Gly Glu His Tyr Phe Glu Phe Gln Gln Gly
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 188

Gly Glu His Tyr Phe Glu Phe Ala Pro Gly Gly
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 189

Gly Gln Gln His Tyr Phe Glu Phe Glu Lys Gly
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (7)..(7)
<223> OTHER INFORMATION: X is T or S
<220> FEATURE:
<221> NAME/KEY: MISC_FEATURE
<222> LOCATION: (9)..(9)
<223> OTHER INFORMATION: X is Q or A

<400> SEQUENCE: 190

Gln Gly Glu His Tyr Phe Xaa Phe Xaa Gln Pro
```

```
<210> SEQ ID NO 191
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (6)..(6)
<223> OTHER INFORMATION: X is T or S

<400> SEQUENCE: 191

Gly Glu His Tyr Phe Xaa Phe Glu Pro Ala Gly
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MISC_FEATURE
<222> LOCATION: (2)..(2)
<223> OTHER INFORMATION: X is Q or G
<220> FEATURE:
<221> NAME/KEY: MISC_FEATURE
<222> LOCATION: (3)..(3)
<223> OTHER INFORMATION: X is Q or G
<220> FEATURE:
<221> NAME/KEY: MISC_FEATURE
<222> LOCATION: (10)..(10)
<223> OTHER INFORMATION: X is Q or A

<400> SEQUENCE: 192

Xaa Xaa Xaa His Tyr Phe Glu Phe Glu Xaa
1               5                   10

<210> SEQ ID NO 193
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 193

Xaa Xaa Trp Lys Ala Glu Lys Xaa Xaa
1               5

<210> SEQ ID NO 194
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 194
```

Gly Phe Gly Trp Lys Ala Glu Lys Phe Asn Gly
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (2)..(2)
<223> OTHER INFORMATION: X is F or W or Y
<220> FEATURE:
<221> NAME/KEY: MISC_FEATURE
<222> LOCATION: (7)..(7)
<223> OTHER INFORMATION: X is E or D

<400> SEQUENCE: 195

Gly Xaa Gly Trp Lys Thr Xaa Lys Phe Asn Ser
1               5                   10

<210> SEQ ID NO 196
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 196

Xaa Xaa Trp Asp Trp Asp Trp Xaa Xaa
1               5

<210> SEQ ID NO 197
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 197

Lys Lys Trp Asp Trp Asp Trp Lys Trp
1               5

<210> SEQ ID NO 198
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 198

Gly Arg Ser Trp Asp Trp Asp Trp Lys Lys Gly
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Synthetic Peptide Sequence

```
<400> SEQUENCE: 199

Gly Lys Lys Trp Asp Trp Asp Trp Lys Trp Gly
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (5)..(5)
<223> OTHER INFORMATION: X is D or E
<220> FEATURE:
<221> NAME/KEY: MISC_FEATURE
<222> LOCATION: (7)..(7)
<223> OTHER INFORMATION: X is D or E

<400> SEQUENCE: 200

Gly Arg Ser Trp Xaa Trp Xaa Trp Lys Lys Thr
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (7)..(7)
<223> OTHER INFORMATION: X is D or E

<400> SEQUENCE: 201

Tyr Gln Leu Phe Asp Trp Xaa Trp Lys Lys Thr
1               5                   10

<210> SEQ ID NO 202
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 202

Xaa Xaa Trp Lys Glu Asp Trp Xaa Xaa
1               5

<210> SEQ ID NO 203
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 203

Gly Tyr Lys Trp Lys Glu Asp Trp Lys Trp Gly
1               5                   10

<210> SEQ ID NO 204
```

```
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (6)..(6)
<223> OTHER INFORMATION: X is D or E
<220> FEATURE:
<221> NAME/KEY: MISC_FEATURE
<222> LOCATION: (7)..(7)
<223> OTHER INFORMATION: X is D or E

<400> SEQUENCE: 204

Phe Gly Lys Trp Lys Xaa Xaa Asn Lys Trp Gly
1               5                   10

<210> SEQ ID NO 205
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 205

Xaa Xaa Trp Thr Lys Val Lys Xaa Xaa
1               5

<210> SEQ ID NO 206
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 206

Gly Tyr Glu Trp Thr Lys Val Lys Asn Tyr Gly
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 207

Gly Tyr Ser Trp Thr Lys Val Lys Asp Tyr Gly
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 208

Gly Tyr Glu Trp Thr Lys Tyr Lys Asn Tyr Gly
1               5                   10
```

<210> SEQ ID NO 209
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (9)..(9)
<223> OTHER INFORMATION: X is D or E

<400> SEQUENCE: 209

Gly Tyr Ser Trp Asn Lys Tyr Lys Xaa Tyr Gly
1               5                   10

<210> SEQ ID NO 210
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 210

Xaa Xaa Asn Ala Tyr Phe Ser Xaa Xaa
1               5

<210> SEQ ID NO 211
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 211

Phe Asp Asn Ala Tyr Phe Ser Gly Asn
1               5

<210> SEQ ID NO 212
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 212

Asn Gln Asn Ala Tyr Phe Ser Gly Asn Gly
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 213

Gly Tyr Glu Asn Ala Tyr Phe Ser Gly Ser Gly
1               5                   10

<210> SEQ ID NO 214

```
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 214

Gly Phe Asp Asn Ala Tyr Phe Ser Gly Asn Gly
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 215

Gly Asn Gln Asn Ala Tyr Phe Ser Gly Asn Gly
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (1)..(1)
<223> OTHER INFORMATION: X is G or T
<220> FEATURE:
<221> NAME/KEY: MISC_FEATURE
<222> LOCATION: (3)..(3)
<223> OTHER INFORMATION: X is E or D
<220> FEATURE:
<221> NAME/KEY: MISC_FEATURE
<222> LOCATION: (10)..(10)
<223> OTHER INFORMATION: X is S or N
<220> FEATURE:
<221> NAME/KEY: MISC_FEATURE
<222> LOCATION: (11)..(11)
<223> OTHER INFORMATION: X is G or N

<400> SEQUENCE: 216

Xaa Tyr Xaa Asn Ala Tyr Phe Ser Gly Xaa Xaa
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (3)..(3)
<223> OTHER INFORMATION: X is D or E

<400> SEQUENCE: 217

Thr Gln Xaa Asn Ala Tyr Phe Ser Gly Asn Gly
1               5                   10

<210> SEQ ID NO 218
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
```

```
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 218

Xaa Xaa Asn Asp Lys Phe Ser Xaa Xaa
1               5

<210> SEQ ID NO 219
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 219

Gly Gly Val Gln Asn Asp Lys Phe Ser Gly Ser
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (4)..(4)
<223> OTHER INFORMATION: X is W or Y

<400> SEQUENCE: 220

Gly Val Val Xaa Asn Asp Lys Phe Ser Gly Asn
1               5                   10

<210> SEQ ID NO 221
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 221

Xaa Xaa His Glu Thr Ala Arg Xaa Xaa
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 222

Cys Ala His Glu Thr Ala Arg Trp Ala
1               5

<210> SEQ ID NO 223
<211> LENGTH: 11
```

```
<212> TYPE: PRT
<213> ORGANISM: Artificial Sequence
<220> FEATURE:
<223> OTHER INFORMATION: Synthetic Peptide Sequence

<400> SEQUENCE: 223

Gly Cys Ala His Glu Thr Ala Arg Trp Ala Gly
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 224

Gly Cys Gly His Glu Thr Ala Arg Asn Trp Gly
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (10)..(10)
<223> OTHER INFORMATION: X is W or Y

<400> SEQUENCE: 225

Gly Cys Xaa His Glu Thr Ala Arg Asn Xaa Gly
1               5                   10

<210> SEQ ID NO 226
<211> LENGTH: 9
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 226

Xaa Xaa Arg Ser Glu Lys Phe Xaa Xaa
1               5

<210> SEQ ID NO 227
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 227

Gly Gly Tyr Val Arg Ser Glu Lys Phe Thr Gly
1               5                   10
```

```
<210> SEQ ID NO 228
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 228

Gly Gly Thr Ala Arg Ser Glu Lys Phe Thr Gly
1               5                   10

<210> SEQ ID NO 229
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (4)..(4)
<223> OTHER INFORMATION: X is G or A or Q
<220> FEATURE:
<221> NAME/KEY: MISC_FEATURE
<222> LOCATION: (7)..(7)
<223> OTHER INFORMATION: X is E or D

<400> SEQUENCE: 229

Glu Gly Tyr Xaa Arg Ser Xaa Lys Phe Thr Gly
1               5                   10

<210> SEQ ID NO 230
<211> LENGTH: 11
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (3)..(3)
<223> OTHER INFORMATION: X is T or S
<220> FEATURE:
<221> NAME/KEY: MISC_FEATURE
<222> LOCATION: (4)..(4)
<223> OTHER INFORMATION: X is G or A or Q
<220> FEATURE:
<221> NAME/KEY: MISC_FEATURE
<222> LOCATION: (7)..(7)
<223> OTHER INFORMATION: X is E or D

<400> SEQUENCE: 230

Trp Gly Xaa Xaa Arg Ser Xaa Lys Phe Thr Gly
1               5                   10

<210> SEQ ID NO 231
<211> LENGTH: 5
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: X is F or Y

<400> SEQUENCE: 231

Xaa Asn Asp Lys Xaa
1               5
```

```
<210> SEQ ID NO 232
<211> LENGTH: 6
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 232

Xaa Ser Glu Lys Phe Xaa
1               5

<210> SEQ ID NO 233
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 233

Ser Ala Trp Ser His Pro Gln Phe Glu Lys
1               5                   10

<210> SEQ ID NO 234
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 234

Trp Thr His Pro Gln Phe Glu Gln Lys
1               5

<210> SEQ ID NO 235
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 235

Trp Thr His Pro Gln Phe Glu Gln Pro Lys Ala
1               5                   10

<210> SEQ ID NO 236
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 236

Glu Trp Val His Pro Gln Phe Glu Gln Lys Ala Lys
1               5                   10

<210> SEQ ID NO 237
<211> LENGTH: 11
<212> TYPE: PRT
<213> ORGANISM: Artificial Sequence
<220> FEATURE:
```

```
<223> OTHER INFORMATION: Synthetic Peptide

<400> SEQUENCE: 237

Asn Ser Phe Asp Asp Trp Leu Ala Lys Gly Gly
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 238

Gly Asn Ser Phe Asp Asp Trp Leu Ala Ser Lys Gly
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 239

Ala Asp Tyr Leu Ala Glu Tyr His Gly Gly
1               5                   10

<210> SEQ ID NO 240
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 240

Ala Phe Asp Tyr Leu Ala Gln Tyr His Gly Gly
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 241

Ala Phe Pro Asp Tyr Leu Ala Glu Tyr His Gly Gly
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 242

Asp Pro Ala Pro Ala Trp Ala His Gly Gly
1               5                   10

<210> SEQ ID NO 243
<211> LENGTH: 12
<212> TYPE: PRT
<213> ORGANISM: Artificial Sequence
<220> FEATURE:
<223> OTHER INFORMATION: Synthetic Peptide
```

<400> SEQUENCE: 243

Arg Asp Pro Ala Pro Ala Trp Ala His Gly Gly Gly
1               5                   10

SPECIFIC PEPTIDE BINDERS TO PROTEINS IDENTIFIED VIA SYSTEMATIC DISCOVERY, MATURATION AND EXTENSION PROCESS

BACKGROUND OF THE INVENTION

Understanding protein-protein interactions is important for basic research as well as various biomedical and other practical applications. Examples of this kind include binding between peptide fragments or epitopes and antibodies, the interaction between proteins and short fragments of other proteins, for example, MDM2 and p53 transactivation domain, Bcl-xL and Bak peptide, as well as binding between peptides referred to as aptamers to their target proteins. Development of simple and reliable methods of identifying peptide binders for proteins would help to understand the mechanisms of protein-protein interaction and open new opportunities for drug discovery.

State of the art in silico peptide discovery is guided by the X-ray crystal structures and relies on existing structural information. The application of such methods to de novo discovery of peptide binders is limited. To date, experimental methods provided the most effective approaches for peptide discovery. One approach to identification binders to proteins is the display technology that relies on combinatorial peptide libraries in which peptides are linked to DNA or RNA molecules encoding them. The libraries are panned against immobilized target protein to identify few abundant sequences or so called "winners." Selection procedure is performed in several rounds. After each round, the sequences of selected peptides are deduced by PCR amplification of the encoding nucleic acid sequences. Different variations of this approach have been developed and successfully applied to peptide discovery; the most commonly used are phage display, ribosome display, and mRNA-display methods. Despite the unquestionable success of these methods at identifying peptide binders, they are expensive, time consuming and prone to contamination. Furthermore, the existing methods do not ensure that the top selected peptide binders are indeed the best and most specific binders and whether they can be improved. First, there is no mechanism that discriminates between specific binders and non-specific ones in the display methods. Second, selecting only a few "winners" prevents display methods from identifying other potentially strong binders that may have had a disadvantage in the selection process. Third, the display methods require careful optimization of the selection conditions for each target protein. Currently, there is no systematic approach that allows selecting an optimal binder for a particular target. Instead, laborious trial and error optimization techniques are used. The present invention addresses this need by providing a systematic approach to fast and reliable discovery of multiple specific binders for a variety of target proteins.

An alternative to display methods to study peptide-protein interactions are peptide arrays. Peptide arrays could be made of peptides synthesized using solid phase peptide synthesis and then immobilized on solid support or could be directly prepared by in situ synthesis methods. Although peptide arrays are commercially available, their application is limited by a relatively low density and high cost of manufacturing. Both of these issues can be addressed by use of maskless light-directed technology, see (Pellois, Zhou et al. (2002) *Individually addressable parallel peptide synthesis on microchips*) and U.S. Pat. No. 6,375,903. The microarrays are generally synthesized by using light to direct which oligonucleotides or peptides are synthesized at specific locations on an array, these locations being called features. MAS-based microarray synthesis technology allows for the parallel synthesis of millions of unique oligonucleotide or peptide features in a very small area of a standard microscope slide.

Specific peptide binders have multiple applications, including medical diagnostics, drug discovery and biotechnology. The present invention comprises a series of binders to biologically relevant target proteins, identified by an alternative method of fast and reliable discovery of highly-specific peptide binders.

SUMMARY OF THE INVENTION

The instant disclosure provides a series of peptide binders to biologically relevant proteins identified by a method that comprise identification of overlapping binding of the target protein to small peptides among a comprehensive population of peptides immobilized on a microarray, then performing one or more rounds of maturation of the isolated core hit peptides, followed by one or more rounds of N-terminal and C-terminal extension of the matured peptides The invention provides novel peptide binders for streptavidin (SA), Taq polymerase and several human proteins: Prostate Specific Antigen (PSA), thrombin, Tumor Necrosis Factor Alpha (TNFα), and Urokinase-type Plasminogen Activator (uPA).

In one embodiment, the invention is a peptide binder to a protein selected from streptavidin (SA), Taq polymerase, human Prostate Specific Antigen (PSA), human thrombin, human Tumor Necrosis Factor Alpha (TNFα), and human Urokinase-type Plasminogen Activator (uPA), identified by a method comprising the steps of: exposing the protein to an array comprising a first population of peptide binders, whereby the protein binds to at least one peptide binder comprising the population; identifying overlap in peptide binder sequences comprising the population which bind the protein, whereby a core binder sequence is determined; performing at least one alteration selected from a single amino acid substitution, a double amino acid substitution, an amino acid deletion, and an amino acid insertion of amino acids comprising the core binder sequence, whereby a second population of core binder sequences is generated; exposing the second population to the protein, whereby the protein binds to at least one peptide sequence of the second population; identifying one or more sequences of the second population demonstrating strong binding properties to the protein, whereby a matured core binder sequence is determined; performing at least one of N-terminal and C-terminal extension of the matured core binder sequence determined in step e, whereby a population of matured extended peptide binders is generated; exposing the protein to an array comprising the population of matured peptide binders; and identifying overlap in the N-terminal or C-terminal peptide binder sequences of the peptides comprising the population of mature peptide binders, whereby an extended, matured core peptide binder sequence is determined as a streptavidin binder comprising a sequence selected from the sequences in Tables 1 and 2; or a Taq polymerase binder comprising a sequence selected from the sequences in Table 3; or binder to Prostate Specific Antigen (PSA) comprising a sequence selected from the sequences in Table 4; or a thrombin binder comprising a sequence selected from the sequences in Table 5; or binder to Tumor Necrosis Factor comprising a sequence selected from the sequences in Table 6; or binder to Urokinase-type Plasminogen Activator (uPA) comprising a sequence selected from the sequences in Table 7.

In some embodiments, the invention is an artificial peptide binder to streptavidin comprising a sequence selected from Table 1 (LGEYH (SEQ ID NO:1), FDEWL (SEQ ID NO:2), PAWAH (SEQ ID NO:3), DPFGW (SEQ ID NO:4), and RPGWK (SEQ ID NO:5)) or consisting of a sequence selected from Table 2 (DYLGEYHGG (SEQ ID NO:6), NSFDEWLNQ (SEQ ID NO:7), NSFDEWLQK (SEQ ID NO:8), NSFDEWLAN (SEQ ID NO:9), PAPAWAHGG (SEQ ID NO:10), RAPAWAHGG (SEQ ID NO:11), SGDPFGWST (SEQ ID NO:12), RPGWKLW (SEQ ID NO:13)).

In some embodiments, the invention is an artificial peptide binder to Taq polymerase of claim 1, comprising a sequence selected from Table 3 (HEFSF (SEQ ID NO:14), HYFEF (SEQ ID NO:19), WKAEK (SEQ ID NO:26), WDWDW (SEQ ID NO:29), WKEDW (SEQ ID NO:32), WTKVK (SEQ ID NO:35)) or consisting of a sequence selected from Table 3 (FQQHEFSFAQQ (SEQ ID NO:17), GQHEFSFGPAI (SEQ ID NO:18), AQGHYFEFEKQ (SEQ ID NO:23), QGEHYFTFQQP (SEQ ID NO:24), GEHYFTFEPAG (SEQ ID NO:25), FGWKTEKFNS (SEQ ID NO:28), RSWDWDWKKT (SEQ ID NO:31), FGKWKEDNKW (SEQ ID NO:34), YEWTKYKNY (SEQ ID NO:38), YSWNKYKDY (SEQ ID NO:39)).

In some embodiments, the invention is an artificial peptide binder to Prostate Specific Antigen (PSA) of claim 1, comprising a sequence from Table 4 (FEVYL (SEQ ID NO:40), WTVYA (SEQ ID NO:45), WEVHL (SEQ ID NO:51), RSILY (SEQ ID NO:54)) or consisting of a sequence selected from Table 4 (GQFEVYIPGA (SEQ ID NO:43), TDFEVYFPKT (SEQ ID NO:44), ASEWTVYAGN (SEQ ID NO:48), AGDWTVYAGLG (SEQ ID NO:49), ALDWQVYAGFG (SEQ ID NO:50), GTGWEVHLGK (SEQ ID NO:53), QSCRSILYGD (SEQ ID NO:56)).

In some embodiments, the invention is an artificial peptide binder to thrombin of claim 1, comprising a sequence selected from Table 5 (PINLG (SEQ ID NO:57), VPIRL (SEQ ID NO:60), WPINL (SEQ ID NO:62), APVRL (SEQ ID NO:65), RQIFL (SEQ ID NO:67). PIRLK (SEQ ID NO:69), PVGSR (SEQ ID NO:72), RDPGR (SEQ ID NO:75)) or consisting of a sequence selected from Table 5 (WAPINLGQR (SEQ ID NO:58), PAPINLGNR (SEQ ID NO:59), YAVPIRLGA (SEQ ID NO:61), RYWPINLGK (SEQ ID NO:63), YRWPINLGK (SEQ ID NO:64), KYAPVRLGS (SEQ ID NO:66), DGRQIFLQK (SEQ ID NO:68), NWPIRLKPA (SEQ ID NO:70), YAPIRLKPQ (SEQ ID NO:71), GWPVGSRQY (SEQ ID NO:73), YGPVGSRGF (SEQ ID NO:74), ENRDPGRSF (SEQ ID NO:76)).

In some embodiments, the invention is an artificial peptide binder to Tumor Necrosis Factor alpha (TNFα) of claim 1, comprising a sequence selected from Table 6 (AIAIF (SEQ ID NO:77), TAVFV (SEQ ID NO:83), ALYLF (SEQ ID NO:88), VTVYV (SEQ ID NO:91)) or consisting of a sequence selected from Table 6 (GPAVAIFGG (SEQ ID NO:80), EAAVAIFGG (SEQ ID NO:81), QAAVAIFGD (SEQ ID NO:82), GGTAVFVVNT (SEQ ID NO:86), DSTAVFVNT (SEQ ID NO:87), QGALYLFGD (SEQ ID NO:90), TSVTVWVNN (SEQ ID NO:94), QSVSVYVNT (SEQ ID NO:95)).

In some embodiments, the invention is an artificial peptide binder to Urokinase-type Plasminogen Activator (uPA) of claim 1, comprising a sequence selected from Table 7 (NAYFS (SEQ ID NO:96), NDKFS (SEQ ID NO:100), YNDKF (SEQ ID NO:101), HETAR (SEQ ID NO:105), RSEKF (SEQ ID NO:108)) or consisting of a sequence selected from Table 7 (YENAYFSGSG (SEQ ID NO-98), QENAYFSGNG (SEQ ID NO:99), WGVQNDKFSGS (SEQ ID NO:103), VVWNDKFSGN (SEQ ID NO:104), CAHETARNW (SEQ ID NO:107), EGYGRSEKFT (SEQ ID NO:111), WGTGRSEKFT (SEQ ID NO:112)).

In some embodiments, the invention is a composition, comprising a peptide having at least 80% sequence identity to the peptide RDPAPAWAHGGG (SEQ ID NO:243). A complex of the peptide with a molecule of streptavidin has an equilibrium dissociation constant ($K_D$) of less than 10 micromolar (µM).

In some embodiments, the invention is a composition, comprising a peptide having at least 80% sequence identity to the peptide AFPDYLAEYHGG (SEQ ID NO:241). A complex of the peptide with a molecule of streptavidin has an equilibrium dissociation constant ($K_D$) of less than about 100 micromolar (µM).

DETAILED DESCRIPTION OF THE INVENTION

I. Peptides

Figure 1:
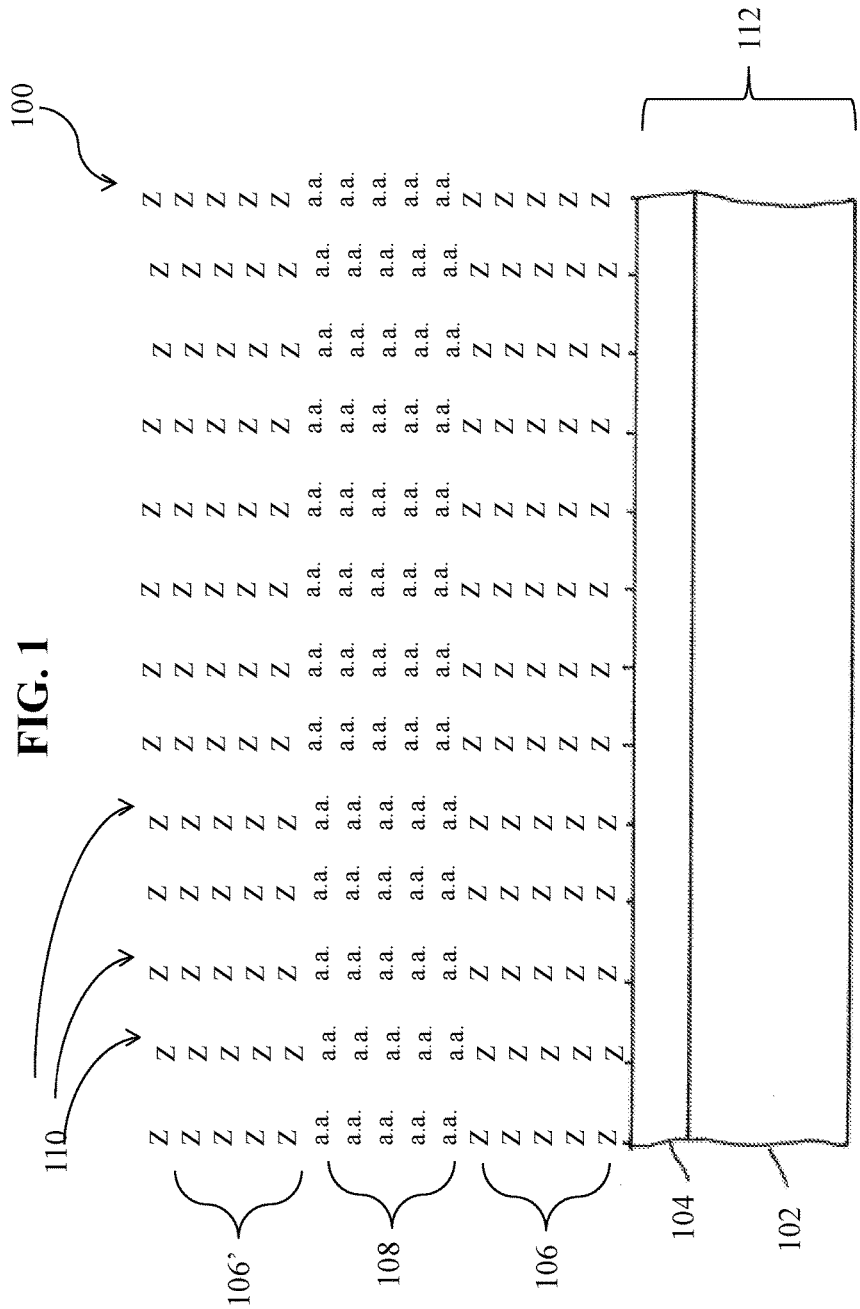
FIG. 1 is a schematic view illustrating arrays comprising peptide probes thereon in accordance with the present disclosure.

According to various embodiments of the instant disclosure, novel peptides ("peptide binders") are disclosed. Each of the peptides has applications in the life science and healthcare fields. In examples described herein, a linear form of peptides is shown. However, one of skill in the art would immediately appreciate that the peptides can be converted to a cyclic form, e.g., by reacting the N-terminus with the C-terminus as disclosed in the U.S. application Ser. No. 14/577,334 filed on Dec. 19, 2014. The embodiments of the invention therefore include both cyclic binder peptides and linear binder peptides.

As used herein, the terms "peptide," "oligopeptide" or "peptide binder" refer to organic compounds composed of amino acids, which may be arranged in either a linear chain (joined together by peptide bonds between the carboxyl and amino groups of adjacent amino acid residues), in a cyclic form (cyclized using an internal site) or in a constrained (e.g., "macrocycle" of head-to-tail cyclized form). The terms "peptide" or "oligopeptide" also refer to shorter polypeptides, i.e., organic compounds composed of less than 50 amino acid residues. A macrocycle (or constrained peptide), as used herein, is used in its customary meaning for describing a cyclic small molecule such as a peptide of about 500 Daltons to about 2,000 Daltons.

The term "natural amino acid" refers to one of the 20 amino acids typically found in proteins and used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine, and lysine. The term "all 20 amino acids" refers to the 20 natural amino acids listed above.

The term "non-natural amino acid" refers to an organic compound that is not among those encoded by the standard genetic code, or incorporated into proteins during translation. Therefore, non-natural amino acids include amino acids or analogs of amino acids, but are not limited to, the D-isostereomers of amino acids, the beta-amino-analogs of amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

According to embodiments of the instant disclosure, candidate peptide binders are presented immobilized on a support surface (e.g., a microarray). The initially selected peptide binders optionally undergo one or more rounds of extension and maturation processes to yield the binders disclosed herein.

II. Microarrays

The peptide binders disclosed herein are generated using oligopeptide microarrays. As used herein, the term "microarray" refers to a two dimensional arrangement of features on the surface of a solid or semi-solid support. A single microarray or, in some cases, multiple microarrays (e.g., 3, 4, 5, or more microarrays) can be located on one solid support. For a solid support having fixed dimensions, the size of the microarrays depends on the number of microarrays on the solid support. That is, the higher the number of microarrays per solid support, the smaller the arrays have to be to fit on the solid support. The arrays can be designed in any shape, but preferably they are designed as squares or rectangles. The ready to use product is the oligopeptide microarray on the solid or semi-solid support (microarray slide).

The terms "peptide microarray" or "oligopeptide microarray," or "peptide chip," or "peptide epitope microarray" refer to a population or collection of peptides displayed on a microarray, i.e., a solid surface, for example a glass, carbon composite or plastic array, slide or chip.

The term "feature" refers to a defined area on the surface of a microarray. The feature comprises biomolecules, such as peptides, nucleic acids, carbohydrates, and the like. One feature can contain biomolecules with different properties, such as different sequences or orientations, as compared to other features. The size of a feature is determined by two factors: i) the number of features on an array, the higher the number of features on an array, the smaller is each single feature, ii) the number of individually addressable aluminum mirror elements which are used for the irradiation of one feature. The higher the number of mirror elements used for the irradiation of one feature, the bigger is each single feature. The number of features on an array may be limited by the number of mirror elements (pixels) present in the micro mirror device. For example, the state of the art micromirror device from Texas Instruments, Inc. (Dallas, Tex.) currently contains 4.2 million mirror elements (pixels), thus the number of features within such exemplary microarray is therefore limited by this number. However, higher density arrays are possible with other micromirror devices.

The term "solid or semi-solid support" refers to any solid material, having a surface area to which organic molecules can be attached through bond formation or absorbed through electronic or static interactions such as covalent bonds or complex formation through a specific functional group. The support can be a combination of materials such as plastic on glass, carbon on glass, and the like. The functional surface can be simple organic molecules but can also comprise of co-polymers, dendrimers, molecular brushes, and the like.

The term "plastic" refers to synthetic materials, such as homo- or hetero-co-polymers of organic building blocks (monomer) with a functionalized surface such that organic molecules can be attached through covalent bond formation or absorbed through electronic or static interactions such as through bond formation through a functional group. Preferably the term "plastic" refers to polyolefin, which is a polymer derived by polymerization of an olefin (e.g., ethylene propylene diene monomer polymer, polyisobutylene). Most preferably, the plastic is a polyolefin with defined optical properties, like TOPAS® (TOPAS Advanced Polymers, Inc., Florence, Ky.) or ZEONOR/EX® (ZEON Chem., Louisville, Ky.).

The term "functional group" refers to any of numerous combinations of atoms that form parts of chemical molecules, that undergo characteristic reactions themselves, and that influence the reactivity of the remainder of the molecule. Typical functional groups include, but are not limited to, hydroxyl, carboxyl, aldehyde, carbonyl, amino, azide, alkynyl, thiol, and nitril. Potentially reactive functional groups include, for example, amines, carboxylic acids, alcohols, double bonds, and the like. Preferred functional groups are potentially reactive functional groups of amino acids such as amino groups or carboxyl groups.

Various methods for the production of oligopeptide microarrays are known in the art. For example, spotting prefabricated peptides or in-situ synthesis by spotting reagents, e.g., on membranes, exemplify known methods. Other known methods used for generating peptide arrays of higher density are the so-called photolithographic techniques, where the synthetic design of the desired biopolymers is controlled by suitable photolabile protecting groups (PLPG) releasing the linkage site for the respective next component (amino acid, oligonucleotide) upon exposure to electromagnetic radiation, such as light (Fodor et al., (1993) *Nature* 364:555-556; Fodor et al., (1991) *Science* 251:767-773). Two different photolithographic techniques are known in the state of the art. The first is a photolithographic mask, used to direct light to specific areas of the synthesis surface effecting localized deprotection of the PLPG. "Masked" methods include the synthesis of polymers utilizing a mount (e.g., a "mask") which engages a substrate and provides a reactor space between the substrate and the mount. Exemplary embodiments of such "masked" array synthesis are described in, for example, U.S. Pat. Nos. 5,143,854 and 5,445,934, the disclosures of which are hereby incorporated by reference. Potential drawbacks of this technique, however, include the need for a large number of masking steps resulting in a relatively low overall yield and high costs, e.g., the synthesis of a peptide of only six amino acids in length could require over 100 masks. The second photolithographic technique is the so-called maskless photolithography, where light is directed to specific areas of the synthesis surface effecting localized deprotection of the PLPG by digital projection technologies, such as micromirror devices (Singh-Gasson et al., *Nature Biotechn.* 17 (1999) 974-978). Such "maskless" array synthesis thus eliminates the need for time-consuming and expensive production of exposure masks. It should be understood that the embodiments of the systems and methods disclosed herein may comprise or utilize any of the various array synthesis techniques described above.

The use of PLPG (photolabile protecting groups), providing the basis for the photolithography based synthesis of oligopeptide microarrays, is well known in the art. Commonly used PLPG for photolithography based biopolymer synthesis are for example α-methyl-6-nitropiperonyl-oxycarbonyl (MeNPOC) (Pease et al., *Proc. Nati. Acad. Sci. USA* (1994) 91:5022-5026), 2-(2-nitrophenyl)-propoxycarbonyl (NPPOC) (Hasan et al. (1997) *Tetrahedron* 53: 4247-4264), nitroveratryloxycarbonyl (NVOC) (Fodor et al. (1991) *Science* 251:767-773) and 2-nitrobenzyloxycarbonyl (NBOC).

Amino acids have been introduced in photolithographic solid-phase peptide synthesis of oligopeptide microarrays, which were protected with NPPOC as a photolabile amino protecting group, wherein glass slides were used as a support (U.S. App. Pub. No. 20050101763). The method using NPPOC protected amino acids has the disadvantage that the half-life upon irradiation with light of all (except one) protected amino acids is within the range of approximately 2 to 3 minutes under certain conditions. In contrast, under the same conditions, NPPOC-protected tyrosine exhibits a half-life of almost 10 minutes. As the velocity of the whole synthesis process depends on the slowest sub-process, this phenomenon increases the time of the synthesis process by a factor of 3 to 4. Concomitantly, the degree of damage by photogenerated radical ions to the growing oligomers increases with increasing and excessive light dose requirement.

As understood by one of skill in the art, peptide microarrays comprise an assay principle whereby thousands (or in the case of the instant disclosure, millions) of peptides (in some embodiments presented in multiple copies) are linked or immobilized to the surface of a solid support (which in some embodiments comprises a glass, carbon composite or plastic chip or slide).

In some embodiments, the peptide microarray exposed to the protein of interest undergoes one or more washing steps, and then is subjected to a detection process. In some embodiments, the array is exposed to an antibody targeting the protein of interest (e.g. anti IgG human/mouse or anti-phosphotyrosine or anti-myc). Usually, the secondary antibody is tagged by a fluorescent label that can be detected by a fluorescence scanner. Other detection methods are chemiluminescence, colorimetry, or autoradiography. In other embodiments, the protein of interest is biotinylated, and then detected by streptavidin conjugated to a fluorophore. In yet other embodiments, the protein of interest is tagged with specific tags, such as His-tag, Flag-tag, myc-tag, etc., and detected with a fluorophore-conjugated antibody specific for the tag.

After scanning the microarray slides, the scanner records a 20-bit, 16-bit or 8-bit numeric image in tagged image file format (*.tif). The .tif-image enables interpretation and quantification of each fluorescent spot on the scanned microarray slide. This quantitative data is the basis for performing statistical analysis on measured binding events or peptide modifications on the microarray slide. For evaluation and interpretation of detected signals an allocation of the peptide spot (visible in the image) and the corresponding peptide sequence has to be performed.

A peptide microarray is a slide with peptides spotted onto it or assembled directly on the surface by in-situ synthesis. Peptides are ideally covalently linked through a chemoselective bond leading to peptides with the same orientation for interaction profiling. Alternative procedures include unspecific covalent binding and adhesive immobilization.

According one specific embodiment of the instant disclosure, the specific peptide binders are identified using maskless array synthesis in the fabrication of the peptide binder probes on the substrate. According to such embodiments, the maskless array synthesis employed allows ultra-high density peptide synthesis of up to 2.9 million unique peptides. Each of the 2.9 million features/regions having up to $10^7$ reactive sites that could yield a full-length peptide. Smaller arrays can also be designed. For example, an array representing a comprehensive list of all possible 5-mer peptides using 19 natural amino acids excluding cysteine will have 2,476,099 peptides. In other examples, an array may include non-natural amino acids as well as natural amino acids. An array of 5-mer peptides by using all combinations of 18 natural amino acids excluding cysteine and methionine may also be used. Additionally, an array can exclude other amino acids or amino acid dimers. In some embodiments, an array may be designed to exclude any dimer or a longer repeat of the same amino acid, as well as any peptide containing HR, RH, HK, KH, RK, KR, HP, and PQ sequences to create a library of 1,360,732 unique peptides. Smaller arrays may have replicates of each peptide on the same array to increase the confidence of the conclusions drawn from array data.

In various embodiments, the peptide arrays described herein can have at least $1.6 \times 10^5$ peptides, or up to about $1.0 \times 10^8$ peptides or any number in-between, attached to the solid support of the peptide array. As described herein, a peptide array comprising a particular number of peptides can mean a single peptide array on a single solid support, or the peptides can be divided and attached to more than one solid support to obtain the number of peptides described herein.

Arrays synthesized in accordance with such embodiments can be designed for peptide binder discovery in the linear or cyclic form (as noted herein) and with and without modification such as N-methyl or other post-translational modifications. Arrays are also be designed for further extension of potential binders using a block-approach by performing iterative screens on the N-term and C-term of a potential hit (as is further described in detail herein). Once a hit of an ideal affinity has been discovery it can be further matured using a combination of maturation arrays (described further herein), that allow a combinatorial insertion, deletion and replacement analysis of various amino acids both natural and non-natural.

The peptide arrays of the instant disclosure are used to identify the specific binders of the invention as well as for maturation and extension of the binders.

III. Peptide Binder Discovery

Figure 2:
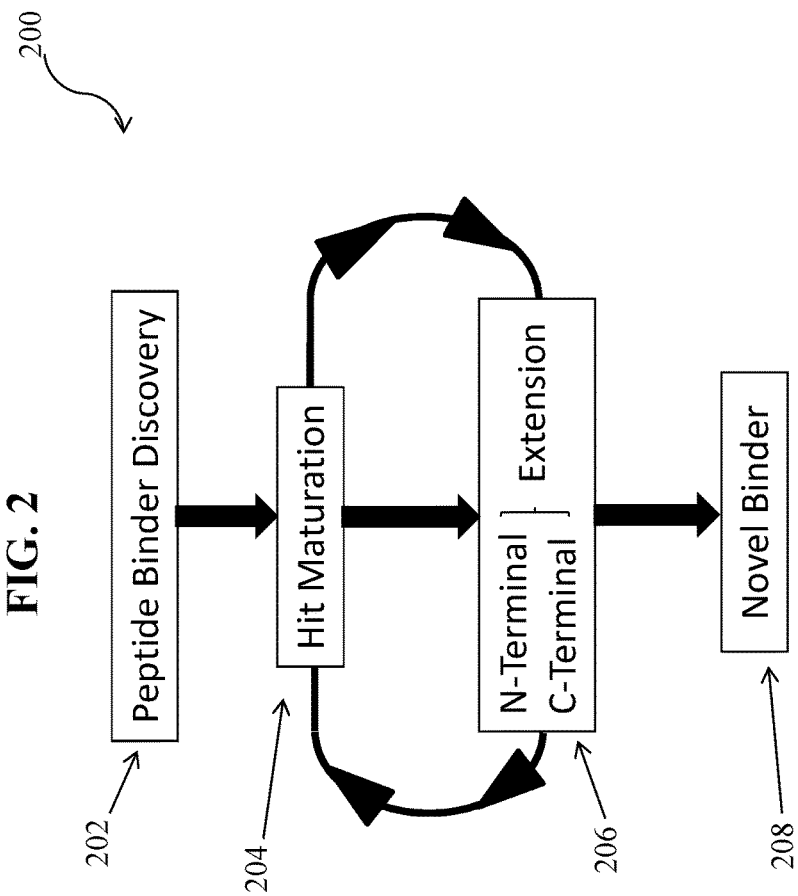
FIG. 2 is a schematic illustration of an embodiment of a process of the present disclosure.

Discovery of novel binders may be accomplished according to the instant disclosure (FIG. 2, the method generally represented as 200). According to some specific embodiments of the instant disclosure, a peptide array may be designed comprising a population of hundreds, thousands, tens of thousands, hundreds of thousands and even millions of peptides. With reference to FIG. 1, in some embodiments, the population of peptides 110 can be configured such that the peptides represent an entire protein, gene, chromosome or even and entire genome of interest (e.g., a human proteome). Additionally, the peptides can be configured according to specific criteria, whereby specific amino acids or motifs are excluded. Furthermore, the peptides can be configured such that each peptide comprises an identical length. For example, in some embodiments the population of peptides 110 immobilized on the array 112 may all comprise 3-, 4-, 5-, 6-, 7-, 8-, 9-, 10-, 11-, or even 12-mers, or more. In some embodiments, the peptides may also each comprise an N-terminal or a C-terminal sequence (for example, 106 and 106') where each peptide comprises both an N and a C terminal peptide sequence of a specific and identical length (e.g., 3-, 4-, 5-, 6-, 7- or even 8- or more peptides).

According to some embodiments, a peptide array 100 is designed including a population of up to 2.9 million peptides 110, configured such that the 2.9 million peptides represents a comprehensive list of all possible 5-mer peptides 108 of a genome, immobilized on an array 112. In some such embodiments, the 5-met peptides 108 (comprising the 2.9 million peptides of the array) may exclude one or more of the 20 amino acids. For example, cysteine (C) could be excluded in order to aid in controlling unusual folding of the peptide. Methionine (M) could be excluded as a rare amino acid within the proteome. Other optional exclusions are amino acid repeats of 2 or more of the same amino acid (in order to aide in controlling non-specific interactions such as charge and hydrophobic interactions); or particular amino acid motifs, e.g., in case of streptavidin binders, those consisting of histidine (H)-proline (P)-glutamine (Q) sequence (which is a known streptavidin binding motif). In some illustrative embodiments, (FIG. 1) the 5-mer peptides 108 may exclude one, or more than one of the exclusions listed above. One embodiment of the invention includes a peptide array comprising a population of up to 2.9 million 5-mer peptides 110, representing the entire human genome, wherein the 5-mer peptides 108 do not include any of the amino acids C and M, do not include amino acid repeats of 2 or more amino acids and do not include the amino acid motif HPQ. Another embodiment of the invention includes a peptide array comprising up to 2.9 million 5-mer peptides, representing the protein content encoded by the entire human genome, wherein the 5-mer peptides do not include any of the amino acids C and M, do not include amino acid repeats of 2 or more amino acids.

It should be understood, that the sequences of the peptides at specific locations on the array are known.

According to further embodiments, each 5-mer peptide 108 comprising the population of up to 2.9 million peptides 110 of the array 100 may be synthesized with 5 cycles of wobble synthesis in each of the N-term of and C-term (see, for example, 106 and 106' FIG. 1). As used herein "wobble synthesis" refers to synthesis (through any of the means disclosed herein) of a sequence of peptides (either constant or random) which are positioned at the N-terminus or C-terminus of the 5-mer peptide 108 of interest. As illustrated in FIG. 1, the specific amino acids comprising the wobble synthesis at either the N- or C-terminal are represented by a "Z." According to various embodiments, wobble synthesis may include any number of peptides at the N-terminus or C-terminus, for example 1, 2, 3, 4, 5, 6, 7, 8, 9, 10 or more, even for example 15 or 20 peptides. Furthermore, wobble synthesis may comprise N-termini and C-termini having the same or differing number of wobble synthesized amino acids.

According to various embodiments, the wobble oligopeptide compositions 106, 106' are flexible in terms of amino acid composition and in term of amino acid ratios/concentrations. For example, the wobble oligopeptide compositions may comprise a mixture of 2 or more amino-acids. An illustrative embodiment of such flexible wobble mix includes a wobble oligopeptide composition 106, 106' of glycine (G) and serine (S) at a ratio of 3:1. Other examples of a flexible wobble mixture include equal concentrations (e.g., equal ratios) of amino acids G, S, adenine (A), vane (V), aspartic acid (D), proline (P), glutamic acid (E), leucine (L), threonine (T) and/or equal concentrations (e.g., equal ratios) of amino acids L, A, D, lysine (K), T, glutamine (Q), P, F, V, tyrosine (Y). Other examples include the wobble oligopeptide compositions 106, 106' comprising any of the 20 known amino acids, in equal concentrations.

As disclosed herein, the wobble oligopeptide synthesis of the various embodiments allow for generating a peptide on an array having a combination of random and directed synthesis amino acids. For example, an oligopeptide probe on an array may comprise a combined 15mer peptide having a peptide sequence in the following format: ZZZZZ-5mer-ZZZZZ, where Z is an amino-acid from a particular wobble oligopeptide mixture.

In some embodiments, a feature may contain $10^7$ peptides. In some such embodiments, the population complexity for each feature may vary depending on the complexity of the wobble mixture. As disclosed herein, creating such complexity using wobble synthesis in a semi-directed synthesis enables the screening of binders on the array, using peptides with diversity up to $10^{12}$ per array. Examples of binder screen for Streptavidin and PSA are set forth below (additional protein targets, e.g., uPA or TNF are also possible according to the methods and systems set forth).

It has further been discovered that linkers 106 (FIG. 1) can vary in length and are optional. In some embodiments, instead of a 5Z linker, a 3Z or a 1Z linker can be used. In such embodiments, Z could be synthesized using a random mixture of all 20 amino acids. It has been discovered that the same target can yield additional 5-mer binder sequences when 1Z linker or no linker is used. It has been discovered that changing the length of or eliminating the linker results in identification of additional peptide binders that were not found using e.g., the original 5Z linker.

In practice, with reference to FIG. 1, an array 100 comprising a solid support 102 having a reactive surface 104 (e.g., a reactive amine layer for example) with a population of peptides 110 (such as a population of 5-mers representing the entire human proteome) immobilized thereto is provided. The exemplary 5-mer peptides comprising the population of peptides 110, according to such embodiment, does not include any of the amino acids C and M, does not include amino acid repeats of 2 or more amino acids and does not include the amino acid motif HPQ. According to such illustrative embodiment, such population of peptides 110 representing the entire human proteome would comprise 1,360,732 individual peptides comprising the population 110. In some embodiments, duplicates or repeats may be placed on the same array. For example, a population 110 comprising a single duplicate would comprise 2,721,464 individual peptides. Additionally, the population of peptides 110 each comprise an N-terminal and C-terminal wobble synthesis oligopeptide 106, 106', which for example consists of five amino acids each consisting of the amino acid glycine and serine in a 3:1 ratio, respectively. The wobble oligopeptides 106, 106' can be omitted or replaced with a single amino acid selected from a random mixture of all 20 amino acids, non-natural amino acids, e.g., 6-amino-hexanoic acid. Some embodiments may include non-amino acid moieties, e.g., polyethylene glycol (PEG).

Referring generally now to step 202 of process 200 of FIG. 2 an exemplary array (e.g. 100 shown in FIG. 1) is exposed to a concentrated, purified protein of interest (as with standard microarray practice), whereby the protein may bind at any of the population of peptides (e.g. 110 shown in FIG. 1), independent of the other peptides comprising the population. After exposure to the protein of interest, binding of the protein of interest to the peptide binders is assayed, for example, by way of exposing the array to an antibody (specific for the protein) which has a reportable label (e.g., peroxidase) attached thereto. Because the peptide sequence of each 5-mer at each location on the array is known, it is possible to chart, or quantify, or compare and contrast the sequences (and binding strengths) of the binding of the protein to specific 5-mer peptide sequences. One such method of comparing the protein binding to the peptides comprising the population is to review the binding in a principled analysis distribution-based clustering, such as described in, *Standardizing and Simplifying Analysis of Peptide Library Data*, Andrew D White et al, J Chem Inf Model, 2013, 53(2), pp 493-499, and illustrated herein. As is exemplified herein, the clustering of protein-5-mer binding (a.k.a., "hits") (shown in a principled analysis distribution-based clustering) indicates 5-mers having overlapping peptide sequences. As demonstrated in greater detail below, from the overlapping peptide sequences (of each cluster), a "core hit" peptide sequence (e.g., a peptide sequence shared by the prominent protein-peptide binding events of the array) can be identified, or at least hypothesized and constructed for further evaluation. (Note it should be understood that an array, as exemplified herein, may identify more than one "core hit" peptide sequence. It should further be understood that it is possible for the "core hit" peptide sequence to comprise more amino acids than, for the example, the 5-mer peptide binders comprising the population of peptides due to possible identification of overlapping and adjacent sequences during principled analysis distribution-based clustering).

IV. Peptide Maturation

Referring now to step 204 of process 200 in FIG. 2, upon identification of a core hit peptide sequence (through the process of peptide binder discovery 202 disclosed, described and exemplified herein), a process of "peptide maturation" 204 whereby the core hit peptide sequence is altered in various ways (through amino acid substitutions, deletions and insertions) at each position of the core hit peptide in order to further optimize/verify the proper core hit sequence. For example, according to some embodiments (for example, where the core hit peptide sequence comprises a given number of, such as 7, amino acids), a maturation array is produced. According to the instant disclosure, the maturation array may have, immobilized thereto, a population of core hit peptides whereby each amino acid in the core hit peptide has undergone an amino acid substitution at each position.

In order to further describe the process of hit maturation 204, an example/hypothetical core hit peptide is described as consisting of a 5-mer peptide having the amino acid sequence -$M_1M_2M_3M_4M_5$-. According to the instant disclosure, hit maturation 204 may involve any of, or a combination of any or all of, amino acid substitutions, deletions and insertions at positions 1, 2, 3, 4 and 5. For example, in regard to the hypothetical core hit peptide -$M_1M_2M_3M_4M_5$-, embodiments of the instant disclosure may include the amino acid M at position 1 being substituted with each of the other 19 amino acids (e.g., $A_1M_2M_3M_4M_5$-, $P_1M_2M_3M_4M_5$-, $V_1M_2M_3M_4M_5$-, $Q_1M_2M_3M_4M_5$-, etc.). Each position (2, 3, 4 and 5) would also have the amino acid M substituted with each of the other 19 amino acids (for example, with position 2 the substitutions would resemble, $M_1A_2M_3M_4M_5$-, $M_1Q_2M_3M_4M_5$-, $M_1P_2M_3M_4M_5$-, $M_1M_2N_3M_4M_5$-, etc.). It should be understood that a peptide (immobilized on an array) is created comprising the substituted and/or deleted and/or inserted sequences of the core hit peptide.

In some embodiments of hit maturation 204 according to the instant disclosure, a double amino acid substitution may be performed. A double amino acid substation includes altering the amino acid at a given position (e.g., a M→P substitution, for example at position 1) and then substituting the amino acid at position 2 with each of the other 19 amino acids the amino acid at position 2. This process is repeated until all possible combinations of positions 1 and 2 are combined. By way of example, referring back to the hypothetical core hit peptide having a 5-mer peptide with amino acid sequence -$M_1M_2M_3M_4M_5$-, a double amino acid substitution with regard to positions 1 and 2 may include, for example, a M-*P substitution at position 1, and then a substation of all 20 amino acids at position 2 (e.g., —$P_1A_2M_3M_4M_5$-, -$P_1F_2M_3M_4M_5$-, -$P_1V_2M_3M_4M_5$-, -$P_1E_2M_3M_4M_5$-, etc.), a M→V substitution at position 1, and then a substation of all 20 amino acids at position 2 (e.g., -$V_1A_2M_3M_4M_5$-, -$V_1F_2M_3M_4M_5$-, -$P_1V_2M_3M_4M_5$-, -$V_1E_2M_3M_4M_5$-, etc.), M→A substitution at position 1, and then a substation of all 20 amino acids at position 2 (e.g., -$A_1A_2M_3M_4M_5$-, -$A_1F_2M_3M_4M_5$-, -$A_1V_2M_3M_4M_5$-, -$A_1E_2M_3M_4M_5$-, etc.).

In some embodiments of hit maturation 204 according to the instant disclosure, an amino acid deletion for each amino acid position of the core hit peptide may be performed. An amino acid deletion includes preparing a peptide including the core hit peptide sequence, but deleting a single amino acid from the core hit peptide sequence (such that a peptide is creating in which the amino acid at each peptide is deleted). By way of example, referring back to the hypothetical core hit peptide having a 5-mer peptide with amino acid sequence -$M_1M_2M_3M_4M_5$-, an amino acid deletion would include preparing a series of peptides having the following sequences -$M_2M_3M_4M_5$-; -$M_1M_3M_4M_5$-; -$M_1M_2M_4M_5$-; -$M_1M_2M_3M_5$-; and -$M_1M_2M_3M_4$-. It should be noted that, following an amino acid deletion of the hypothetical 5-mer, 5 new 4-mers are created. According to some embodiments of the instant disclosure an amino acid substitution or a double amino acid substation scan can be performed for each new 4-mer generated.

Similar to the amino acid deletion scan discussed above, some embodiments of hit maturation 204 disclosed herein may include at amino acid insertion scan, whereby each of the 20 amino acids is inserted before and after every position of the core hit peptide. By way of example, referring back to the hypothetical core hit peptide having a 5-mer peptide with amino acid sequence -$M_1M_2M_3M_4M_5$-, an amino acid insertion scan would include the following sequences, -$XM_1M_2M_3M_4M_5$-; -$M_1XM_2M_3M_4M_5$-; -$M_1M_2XM_3M_4M_5$-; -$M_1M_2M_3XM_4M_5$-; -$M_1M_2M_3M_4XM_5$-; and -$M_1M_2M_3M_4M_5X$- (where X represents an individual amino, selected from the 20 known amino acids or a specific, defined subset of amino acids, whereby a peptide replicate will be created for each of the 20 or defined subset of amino acids).

It should also be understood that the amino acid-substituted peptides, double amino acid-substituted peptides, amino acid deletion scan peptides and amino acid insertion scan peptides described above may also include one, or both of, a N-terminal and C-terminal wobble amino acid sequences (similar to as described at 106, 106' of FIG. 1). As with the N-terminal and C-terminal wobble amino acid sequences described in FIG. 1, the N-terminal and C-terminal wobble amino acid sequences may comprise as few as 1 amino acid or as many as 15 or 20 amino acids, and the N-terminal wobble amino acid sequence may be the same length as, longer than or shorter than the C-terminal wobble amino acid sequence, or be omitted altogether. Further, the N-terminal and C-terminal wobble amino acid sequences may comprise any defined group of amino acids at any given ratios (for example, glycine and serine in a 3:1 ratio, or be a random mixture of all 20 amino acids).

Figure 4:
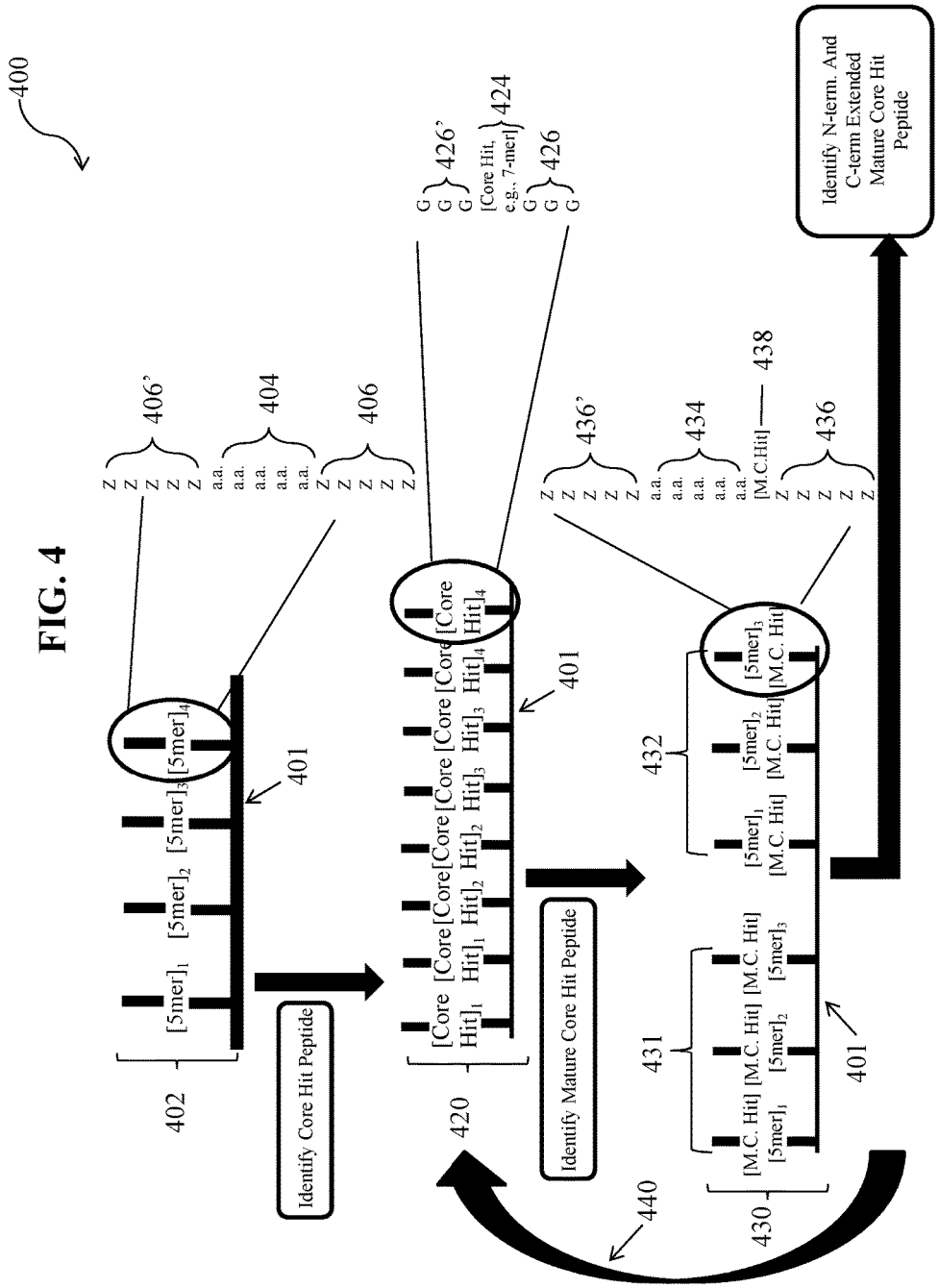
FIG. 4 is a schematic view depicting an embodiment of the process of FIG. 2.

In a specific embodiment of hit maturation 204 described on FIG. 4, a core hit peptide of 7 amino acids (424) undergoes exhaustive single and double amino acid screens, and includes both N-terminal and C-terminal wobble amino acid sequences 426 and 426'. In this example, the terminal sequences comprise three amino acids (all glycine). In other embodiments, different terminal sequences may be added by using different mixtures of amino acids during the maturation process. Any single amino acid can be used or any "mixture consisting of two or more amino acids. In yet other embodiments, a mixture of glycine (G) and serine (S) at a ration 3G:1S is used. In other embodiments, a "random mix" is used consisting of a random mixture of all 20 amino acids. In some embodiments, non-natural amino acids, e.g., 6-amino-hexanoic acid is used. Some embodiments may include non-amino acid moieties, e.g., polyethylene glycol (PEG).

Once the various substitution, deletion and insertion variations of the core hit peptide are prepared (for example, in immobilized fashion on a solid support such as a microarray), the strength of binding of the purified, concentrated target protein is assayed. As shown in the Examples provided below, the process of hit maturation allows for refining the core hit peptide to an amino acid sequence demonstrating the most preferred amino acid sequence for binding the target protein with the highest affinity.

V. Peptide Extension (N-Terminal and C-Terminal)

It is possible that motifs identified in 5-mer array experiments represent only short versions of optimal protein binders. We have developed a strategy of identifying longer motifs by extending sequences selected from 5-mer arrays experiments by one or more amino acids from one or both N- and C-terminus. Starting from a selected peptide and adding one or more amino acids on each terminus, one can create an extension library for further selection. For example, starting from a single peptide and using all 20 natural amino acids, one can create an extension library of 160,000 unique peptides. In some embodiments, each of the extended peptides is synthesized in replicates.

Referring now to step 206 in FIG. 2, upon maturation of the core hit peptide (such that a more optimal amino acid sequence of the core hit peptide is identified for binding the target protein), the N-terminal and/or C-terminal positions undergo an extension step, whereby the length of the matured core hit peptide is further extended for increasing the specificity and affinity for the target peptide.

Figure 3:
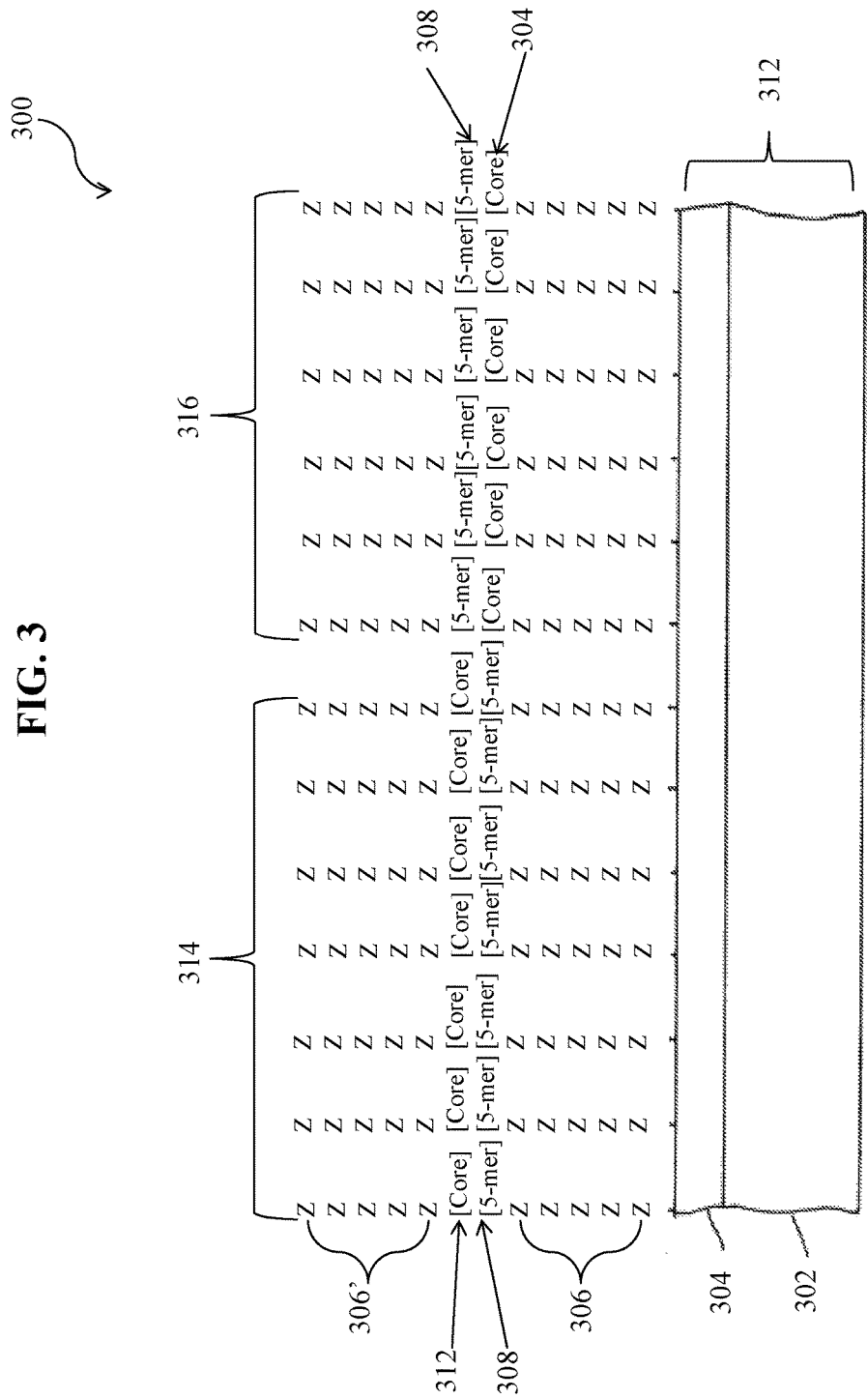
FIG. 3 is a schematic view illustrating another embodiment of an array comprising peptide probes thereon in accordance with the present disclosure.

According to various embodiments of N-terminal extension of the instant disclosure, and with reference to FIG. 3, once the matured core hit peptide sequence 312 is identified through the maturation process (204 of FIG. 2), each specific peptide probe of the population from the peptide binder discovery step (102, FIG. 1) is added (or synthesized onto) the N-terminal end of a matured core hit peptide 312. In this manner, the most C-terminal amino acid of each peptide sequence (108, FIG. 1) is added directly adjacent to the most N-terminal amino acid of the matured core hit peptide 312.

Likewise, according to various embodiments of C-terminal extension of the instant disclosure, and with reference to FIG. 3, once the matured core hit peptide sequence 312 is identified through the maturation process (204 of FIG. 2), each specific peptide probe of the population from the peptide binder discovery step (102, FIG. 1) is added to the C-terminal end of a matured core hit peptide 312. In this manner, the most N-terminal amino acid of each peptide sequence (108, FIG. 1) is added directly adjacent to the most C-terminal amino acid of the matured core hit peptide 312.

According to some embodiments of the instant disclosure (FIG. 3) one or both of the matured core hit peptides used in C-terminal extension and N-terminal extension may also include one or both of a N-terminal and C-terminal wobble amino acid sequence (106, 106' of FIG. 1). As with the N-terminal and C-terminal wobble amino acid sequences described in FIG. 1, the N-terminal and C-terminal wobble amino acid sequences may comprise as few as 1 amino acid or as many as 15 or 20 amino acids (or more), and the N-terminal wobble amino acid sequence may be the same length as, longer than, or shorter than the C-terminal wobble amino acid sequence. Further, the N-terminal and C-terminal wobble amino acid sequences can be added by using different mixtures of amino acids during the maturation process. Any single amino acid can be used or any "wobble mix" consisting of two or more amino acids. In yet other embodiments, a "flexible wobble mix" is used consisting of a mixture of glycine (G) and serine (S) at a ration 3G:1S. In other embodiments, a "random wobble mix" is used consisting of a random mixture of all 20 amino acids. In some embodiments, non-natural amino acids, e.g., 6-aminohexanoic acid can also be used. Some embodiments may include non-amino acid moieties, e.g., polyethylene glycol (PEG).

In FIG. 3, a peptide extension array 300 is shown, having a population of peptides for N-terminal extension 314 and a population of peptides for C-terminal extension 316. Each population of peptides 314, 316 may contain the full population of peptides 110 from peptide array 100 (used in the step of peptide binder discovery 204). As further illustrated, each peptide of both populations of peptides 314, 316 may contain the same matured core peptide 312, each with a different peptide probe 308 (of the population of probes from the peptide binder discovery step 102, FIG. 1). Also as shown in FIG. 3, each peptide of the populations 314, 316 includes N-terminal and C-terminal wobble amino acid sequences.

In some embodiments, the extension array 300 (including populations 314 and 316) is exposed to a concentrated, purified protein of interest (as in peptide binder discovery, step 201 of process 200), whereby the protein may bind any peptide of either population 314, 316, independent of the other peptides comprising the populations 314, 316. After exposure to the protein of interest, binding of the protein of interest to the peptide of the populations 314, 316 is assayed, for example, by way of exposing the complex of the individual peptide of the populations 314, 316 and protein to an antibody (specific for the protein) which has a reportable label (e.g., peroxidase) attached thereto. In another embodiment, the protein of interest may be directly labelled with a reporter molecule. Because the peptide probe sequence 308 (of each 5-mer) for each location on the array, is known, it is possible to chart/quantify/compare/contrast the sequences (and binding strengths) of the binding of the protein to the specific probe comprising the matured core hit peptide 312 with the respective peptide probe 308. An exemplary method of comparing the protein (of interest) binding to the matured core hit peptide 312-peptide probe 308 combination (comprising either population 314 or 316) is to review the binding strength in a principled analysis distribution-based clustering, such as described in *Standardizing and Simplifying Analysis of Peptide Library Data*, Andrew D. White et al., J Chem Inf Model, 2013, 53(2), pp 493-499. As is exemplified herein, clustering of protein binding to the respective probes (of populations 314, 316) shown in a principled analysis distribution-based clustering indicates peptide probe 5-mers 308 having overlapping peptide sequences. As demonstrated in greater detail below, from the overlapping peptide sequences (of each cluster), an extended, matured core hit peptide sequence can be identified, or at least hypothesized and constructed for further evaluation. In some embodiments of the instant application, an extended, matured core hit peptide undergoes a maturation process (as described and exemplified herein and illustrated at step 204 of FIG. 2).

Additional rounds of optimization of extended peptide binders are also possible. For example, a third round of binder optimization may include extension of the sequences identified in the extension array experiments with glycine (G) amino acid. Other optimization may include creating double substitution/deletion libraries that include all possible single and double substitution/deletion variants of the reference sequence, i.e., the peptide binder optimized and selected in any of the previous steps.

VI. Specificity Analysis of Extended, Matured Core Hit Peptide Binders

Following identification of an extended, matured core hit peptide, a specificity analysis may be performed by any method of measuring peptide affinity and specificity available in the art. One example of a specificity analysis includes a "BIACORE™" system analysis which is used for characterizing molecules in terms of the molecules interaction specify to a target, the kinetic rates (of "on," binding, and "off" disassociation) and affinity (binding strength). BIACORE™ is a trademark of General Electric Company and is available via the company website.

FIG. 4 is a brief schematic overview of the method of novel peptide binder identification (e.g., process 200 of FIG. 2). As shown, the peptide binder discovery 402 is performed by preparing (e.g., through maskless array synthesis) a population of peptides on an array 401. As illustrated, each peptide includes 5 "cycles" of N-terminal wobble synthesis 406' and C-terminal wobble synthesis 406 (e.g., both N- and C-terminal wobble synthesis comprises five amino acids). It should be understood that the wobble synthesis of the C- and N-terminal may comprise any composition as noted above (for example, only amino acids G and S, in a 3:1 [G:S] ratio, or a random mixture of all 20 amino acids). Each peptide is also shown as comprising a 5-mer peptide binder 404, which as noted above may comprise up to 2.9 million different peptide sequences such that an entire human proteome is represented. Further, it should be noted that the different peptide binders 404 may be synthesized according to specific "rules" (for example, no C or no M amino acids, no repeats of the same amino acid in consecutive order, or no motifs already known to bind the target protein, e.g., HPQ amino acid motifs for streptavidin). As described above, a protein target of interest (for example, in purified and concentrated form) is exposed to the peptide binders 404, and binding is scored (e.g., by way of a principled clustering analysis), whereby a "core hit peptide" sequence is identified based on overlapping binding motifs.

In some embodiments, upon identification of a core hit peptide sequence, an exhaustive maturation process 420 may be undertaken. In some embodiments, the core hit peptide (exemplified as a 7-mer, 424) is synthesized on an array 401 with both N- and C-terminal wobble (an example shown at step 420 as 3 cycles of N- and C-terminal wobble of only glycine (G) amino acid, although the wobble amino acid may vary as noted above). In some embodiments of exhaustive maturation, a peptide is synthesized on the array 401 wherein every amino acid position of the core hit peptide 424 is substituted with each of the other 19 amino acids or a double amino acid substitution (as described above) is synthesized on the array 401 or an amino acid deletion scan is synthesized on the array 401, or an amino acid insertion scan is synthesized on the array 401. In some cases, all of the above maturation processes are performed (and the repeated as described above for the new peptides generated as a result of the amino acid deletion and insertion scans). Upon synthesis of the maturation array 420 comprising the various peptides (inclusive of the substitutions, deletions and insertions described herein), the target protein is exposed to the modified core hit peptides 424 on the maturation array 420, and strength of binding is assayed, whereby a "matured core hit peptide" sequence is identified.

In further embodiments, after identification of a "matured core hit peptide" sequence, one or both of N- and C-terminal extensions may be performed (shown at 430 as including both N-terminal extension 432 and C-terminal extension 431). N-terminal and C-terminal extensions involve the synthesis of matured core hit peptide having the population of peptide binders 404 (in this example, 5-mers) synthesized at the N-terminal or C-terminal respectively. As shown at 431, C-terminal extension involves five rounds of wobble synthesis 436 and the population of 5-mer peptide binders 434 being synthesized C-terminally of the matured core hit peptide 438 then another 5 cycles of wobble synthesis 436' N-terminally. Similarly, as shown at 432, N-terminal extension involves five rounds of wobble synthesis (as described above) 436 being synthesized C-terminally of the matured core hit peptide 438, then the population of 5-mer peptide binders 434 and another 5 cycles of wobble synthesis 436' synthesized N-terminally (of the matured core hit peptide 438). Upon synthesis of the extension array 430 comprising the various extension peptides (inclusive of C-terminal and N-terminal extension peptides), the target protein is exposed to the C-terminal and N-terminal extension peptide populations 431, 432 synthesized on the extension array 430, and binding is scored (e.g., by way of a principled clustering analysis), whereby a C-terminally, N-terminal extended, matured core hit peptide sequence is identified. As represented by arrow 440, according to some embodiments, after the extended, matured core hit peptide is identified, the maturation process 420 for the extended matured core hit peptide may be repeated and then the extension process may also be repeated for any altered peptide sequence resulting therefrom.

VII. Identification of Binder Peptides for Specific Targets

According to embodiments of the instant disclosure, peptide microarrays are incubated with samples including the target proteins to yield specific binders for streptavidin (SA), Taq polymerase and human proteins: Prostate Specific Antigen (PSA), thrombin, Tumor Necrosis Factor Alpha (TNPFα), and Urokinase-type Plasminogen Activator (uPA).

The invention provides for various uses of the peptide binders. In addition to specific uses indicated below with respect to each type of binder, some uses are common to all binders. For example, for each of the targets listed below, the peptide binders of the present invention may be used as affinity purification or enrichment reagents. In such embodiments, the specific binding of the peptide binder would aid in purification or enrichment of the target protein, e.g., from the patient's sample for diagnostic analysis or from a biosynthetic reactor for obtaining the target molecule in its pure form. In some embodiments, two or more of the multiple binders for the same target can be joined via a linker. The joined binders may affect an avidity-based targeting, avidity being an accumulated strength of multiple affinities.

In yet other embodiments, the binders of the present invention may serve as therapeutic agents. In such embodiments, the peptide binders comprise sequences that have been evolved and selected for optimal binding to their target under physiological conditions, and lack of toxicity.

A. Streptavidin (SA) Binders

In some embodiments, the invention is isolated artificial peptides with specific affinity to streptavidin (SA). In this embodiment, the invention includes peptides consisting of sequences listed in Table 1. The invention further includes peptides comprising sequences listed in Table 1, for example, the peptides consisting of sequences listed in Table 2. In addition to the examples listed in Table 2, shorter or longer peptides (e.g., 5, 6, 7, 8, 9, and up to 20 amino acids) comprising sequences listed in Table 1 are also part of the invention.

TABLE 1

SA binders

Top 5-mer sequences excluding HPQ and HPM motifs

| | |
|---|---|
| LGEYH | (SEQ ID NO: 1) |
| FDEWL | (SEQ ID NO: 2) |
| PAWAH | (SEQ ID NO: 3) |
| DPFGW | (SEQ ID NO: 4) |
| RPGWK | (SEQ ID NO: 5) |

TABLE 2

SA binders

| Core motif | Sequences selected from extension libraries |
|---|---|
| LGEYH (SEQ ID NO: 1) | DYLGEYHGG (SEQ ID NO: 6) |
| FDEWL (SEQ ID NO: 2) | NSFDEWLNQ (SEQ ID NO: 7) |
| | NSFDEWLQK (SEQ ID NO: 8) |
| | NSFDEWLAN (SEQ ID NO: 9) |
| PAWAH (SEQ ID NO: 3) | PAPAWAHGG (SEQ ID NO: 10) |
| | RAPAWAHGG (SEQ ID NO: 11) |
| DPFGW (SEQ ID NO: 4) | SGDPFGWST (SEQ ID NO: 12) |
| RPGWK (SEQ ID NO: 5) | RPGWKLW (SEQ ID NO: 13) |

These novel peptide binders specific for streptavidin can be used in any application where detection or capture of streptavidin, a fragment of streptavidin, or a streptavidin-biotin complex is required. The assays include microarray, immunohistochemistry, chromatography, enzyme-linked immunosorbant assay (ELISA), in situ-hybridization, and assays incorporating one or more nucleotides linked to the novel peptide binders.

For example, the streptavidin binding peptides of the present invention can be used for affinity capture of target molecules comprising the Strep-tag II sequence, see David S. Wilson et al., (2001) *The use of mRNA display to select high-affinity protein-binding peptides* PNAS vol. 98, no. 7, 3750-3755.

In some embodiments, the instant disclosure provides a kit comprising one or more novel peptide binders specific for streptavidin disclosed herein. Such a kit may comprise one or more peptide binders selected from the group listed in Tables 1-2, or a peptide binder comprising any of the sequences selected from the group listed in Tables 1-2.

Taq Polymerase Binders

In some embodiments, the invention is isolated artificial peptides with specific affinity to Taq polymerase. In this embodiment, the invention includes peptides consisting of 5-mer sequences listed in Table 3, column 1. The invention further includes peptides comprising the 5-mer sequences listed in Table 3, column 1, for example, the peptides consisting of sequences listed in Table 3, columns 2 and 3. In addition to the examples listed in Table 3, columns 2 and 3, shorter or longer peptides (e.g., 5, 6, 7, 8, 9, and up to 20 amino acids) comprising sequences listed in Table 3, column 1 are also part of the invention.

TABLE 3

Taq polymerase binders

| Sequences selected from 5-mer libraries | Sequences selected from extension libraries | Sequences selected from substitution/deletion libraries |
|---|---|---|
| HEFSF (SEQ ID NO: 14) | QQHEFSFAQ (SEQ ID NO: 15) | FQQHEFSFAQQ (SEQ ID NO: 17) |
| | GQHEFSFGT (SEQ ID NO: 16) | GQHEFSFGPAI (SEQ ID NO: 18) |
| HYFEF (SEQ ID NO: 19) | GEHYFEFQQ (SEQ ID NO: 20) | AQGHYFEFEKQ (SEQ ID NO: 23) |
| | GEHYFEFAP (SEQ ID NO: 21) | QGEHYFTFQQP (SEQ ID NO: 24) |
| | QOHYFEFEK (SEQ ID NO: 22) | GEHYFTFEPAG (SEQ ID NO: 25) |
| WKAEK (SEQ ID NO: 26) | FGWKAEKFN (SEQ ID NO: 27) | FGWKTEKFNS (SEQ ID NO: 28) |
| WDWDW (SEQ ID NO: 29) | RSWDWDWKK (SEQ ID NO: 30) | RSWDWDWKKT (SEQ ID NO: 31) |
| WKEDW (SEQ ID NO: 32) | YKWKEDWKW (SEQ ID NO: 33) | FGWKEDNKW (SEQ ID NO: 34) |
| WTKVK (SEQ ID NO: 35) | YEWTKVKNY (SEQ ID NO: 36) | YEWTKYKNY (SEQ ID NO: 38) |
| | YSWTKVKDY (SEQ ID NO: 37) | YSWNKYKDY (SEQ ID NO: 39) |

Additional peptide binders to Taq polymerase comprising the 5-mer sequences listed in Table 3, column 1 can be selected by testing candidate peptides in a primer extension assay in the presence of Taq polymerase. The candidates inhibiting the primer extension at ambient temperature but not at a typical PCR extension temperature (between 65 and 75° C.) will be selected. Such inhibition of primer extension at ambient temperatures ("hot start") avoids non-specific amplification of DNA at lower temperatures when non-specific primer annealing and extension may occur. At higher temperatures, only specific (substantially complementary) primer may be extended by the polymerase. At such higher temperature, the specific peptide binder releases inhibition of the polymerase enabling the specific primer extension to occur.

In some embodiments, the invention is a method of amplifying nucleic acids via polymerase chain reaction (PCR) in the presence of one or more peptides comprising sequences listed in Table 3.

B. Prostate Specific Antigen (PSA) Binders

In some embodiments, the invention is isolated artificial peptides with specific affinity to human prostate specific antigen (SA). In this embodiment, the invention includes peptides consisting of sequences listed in Table 4, column 1. The invention further includes peptides comprising sequences listed in Table 4, column 1, for example, the peptides consisting of sequences listed in Table 4, columns 2 and 3. In addition to the examples listed in Table 4, columns 2 and 3, shorter or longer peptides (e.g., 5, 6, 7, 8, 9, and up to 20 amino acids) comprising sequences listed in Table 4, column 1 are also part of the invention.

TABLE 4

PSA binders

| Sequences selected from 5-mer libraries | Sequences selected from extension libraries | Sequences selected from substitution/deletion libraries |
|---|---|---|
| FEVYL (SEQ ID NO: 40) | GQFEVYLPG (SEQ ID NO: 41) | GQFEVYIPGA (SEQ ID NO: 43) |
|  | TDFEVYLPK (SEQ ID NO: 42) | TDFEVYFPKT (SEQ ID NO: 44) |
| WTVYA (SEQ ID NO: 45) | SEWTVYAGN (SEQ ID NO: 46) | ASWTVYAGN (SEQ ID NO: 48) |
|  | GDWTVYAGN (SEQ ID NO: 47) | AGDWTVYAGLG (SEQ ID NO: 49) |
|  |  | ALDWQVYAGFG (SEQ ID NO: 50) |
| WEVHL (SEQ ID NO: 51) | TGWEVHLGK (SEQ ID NO: 52) | GTGWEVHLGK (SEQ ID NO: 53) |
| RSILY (SEQ ID NO: 54) | SCRSILYGQ (SEQ ID NO: 55) | QSCRSILYGD (SEQ ID NO: 56) |

It should be understood that these novel peptide binders specific for PSA can be used in any number of diagnostic assays, including but not limited to microarray, immunohistochemistry (IHC), chromatography, enzyme-linked immunosorbant assay (ELISA), in situ-hybridization, and assays incorporating one or more nucleotides linked to the novel peptide binders. As such, the novel peptide binders disclosed herein may be used in diagnosing prostate cancer in patients.

Furthermore, each novel PSA binder disclosed herein may be combined with one or more additional peptide binders, for example, to form a panel of peptide binders (e.g., as in a multiplexed diagnostic assay). The additional binders may target PSA or other peptides relevant for diagnosis. Such panel may aid in diagnosing prostate cancer or discriminating between prostate cancer and benign prostate hyperplasia. In some embodiments, two or more of the multiple binders targeting PSA can be joined via a linker. The joined binders have increased affinities due to avidity.

The PSA binders of the present invention may be used for enriching the PSA found in the patients sample for any subsequent qualitative or quantitative analysis.

In some embodiments, the invention is a method of diagnostically evaluating a subject for prostate cancer by obtaining a test sample and assaying the sample for PSA with one or more of the novel peptide binders disclosed herein. In some embodiments, PSA within the test sample of the subject is quantified for determining the presence of prostate cancer. Test samples include body fluids, for example, blood, plasma, serum, urine, prostate tissue and prostate fluid (i.e., fluid immediately surrounding the prostate gland). Test samples further include solid tissue or organ samples obtained e.g., by biopsy. Separated cells may be obtained from the body fluids or the tissues or organs by separating techniques such as centrifugation or cell sorting. The sample may be frozen, fresh, fixed (e.g. formalin fixed) or embedded (e.g. paraffin embedded). The sample can be subjected to a variety of well-known post-collection preparative and storage techniques prior to assessing the amount of the marker in the sample.

In one embodiment, the present invention is a method for diagnosing prostate cancer in a subject by determining the presence or amount of PSA in a test sample from the subject. Some embodiments comprise providing a diagnosis of prostate cancer if the amount of PSA in the sample is greater than a reference concentration.

C. Thrombin Binders

In some embodiments, the invention is isolated artificial peptides with specific affinity to human thrombin. In this embodiment, the invention includes peptides consisting of sequences listed in Table 5, column 1. The invention further includes peptides comprising sequences listed in Table 5, column 1, for example, the peptides consisting of sequences listed in Table 5, columns 2 and 3. In addition to the examples listed in Table 5, columns 2 and 3, shorter or longer peptides (e.g., 5, 6, 7, 8, 9, and up to 20 amino acids) comprising sequences listed in Table 5, column 1 are also part of the invention.

TABLE 5

Thrombin binders

| Sequences selected from 5-mer libraries | Sequences selected from extension libraries |
|---|---|
| PINLG (SEQ ID NO: 57) | WAPINLGQR (SEQ ID NO: 58) |
|  | PAPINLGNR (SEQ ID NO: 59) |
| VPIRL (SEQ ID NO: 60) | YAVPIRLGA (SEQ ID NO: 61) |
| WPINL (SEQ ID NO: 62) | RYWPINLGK (SEQ ID NO: 63) |
|  | YRWPINLGK (SEQ ID NO: 64) |
| APVRL (SEQ ID NO: 65) | KYAPVRLGS (SEQ ID NO: 66) |
| RWIFL (SEQ ID NO: 67) | DGRQIFLQK (SEQ ID NO: 68) |

TABLE 5-continued

Thrombin binders

| Sequences selected from 5-mer libraries | Sequences selected from extension libraries |
|---|---|
| PIRLK (SEQ ID NO: 69) | NWPIRLKPA (SEQ ID NO: 70) |
|  | YAPIRLKPQ (SEQ ID NO: 71) |
| PVGSR (SEQ ID NO: 72) | GWPVGSRQY (SEQ ID NO: 73) |
|  | YGPVGSRGF (SEQ ID NO: 74) |
| RDPGR (SEQ ID NO: 75) | ENRDPGRSF (SEQ ID NO: 76) |

Thrombin is a key component in the coagulation pathway. This multi-factor zymogen activation pathway culminates in generation of thrombin which then cleaves fibrinogen to produce fibrin and activates platelets via their thrombin receptors. Thrombin also activates coagulation Factors V, VIII, and XIII, allowing fibrin to form a clot. Elevated levels of thrombin are the cause of thrombosis leading to heart attacks, strokes and pulmonary and venous embolism. (See Esmon, C. T. (2000) *Regulation of blood coagulation*, Biochim. Biophys. Acta 1477:349.) One of the clinical applications of accurate detection of thrombin or levels of thrombin is monitoring patients for the risk of these conditions.

In some embodiments, the invention comprises a method of detecting thrombin or measuring levels of thrombin in a human sample using one or more thrombin-binding peptides disclosed herein. In other embodiments, the invention is a method of monitoring a patient for thromboembolism by detecting thrombin or measuring levels of thrombin in the patient's sample using one or more thrombin-binding peptides disclosed herein. In some embodiments, the invention is a kit for detecting thrombin or measuring levels of thrombin in a human sample, the kit comprising one or more thrombin-binding peptides disclosed herein.

In yet another embodiment, the thrombin-binding peptide disclosed herein is used to bind and inhibit thrombin in a patient. Direct thrombin inhibitors (DTI) and their use to prevent clots are known in the art. Bivalirudin (Angiomax) is a synthetic thrombin-binding peptide related to a natural peptide hirudin found in saliva of the medicinal leech *Hirudo medicinalis*. The present invention provides a method to generate novel thrombin-binding peptides to improve or supplement the existing ability to block thrombin in vive. In this embodiment, the method comprises further evolving and selecting one or more of the thrombin-binding peptide disclosed herein for optimal binding to thrombin under physiological conditions, and lack of toxicity.

D. Tumor Necrosis Factor Alpha (TNFα) Binders

In some embodiments, the invention is isolated artificial peptides with specific affinity to human tumor necrosis factor alpha (TNFα). In this embodiment, the invention includes peptides consisting of sequences listed in Table 6, column 1. The invention further includes peptides comprising sequences listed in Table 6, column 1, for example, the peptides consisting of sequences listed in Table 6, columns 2 and 3. In addition to the examples listed in Table 6, columns 2 and 3, shorter or longer peptides (e.g., 5, 6, 7, 8, 9, and up to 20 amino acids) comprising sequences listed in Table 6, column 1 are also part of the invention.

TABLE 6

TNFα binders

| Sequences selected from 5-mer libraries | Sequences selected from extension libraries | Sequences selected from substitution/deletion libraries |
|---|---|---|
| AIAIF (SEQ ID NO: 77) | GPAIAIFGG (SEQ ID NO: 78) | GPAVAIFGG (SEQ ID NO: 80) |
|  | QAAIAIFGG (SEQ ID NO: 79) | EAAVAIFGG (SEQ ID NO: 81) |
|  |  | QAAVAIFGD (SEQ ID NO: 82) |
| TAVFV (SEQ ID NO: 83) | GGTAVFVNT (SEQ ID NO: 84) | GGTAVFVVNT (SEQ ID NO: 86) |
|  | SSTAVFVNQ (SEQ ID NO: 85) | DSTAVFVNT (SEQ ID NO: 87) |
| ALYLF (SEQ ID NO: 88) | NGALYLFGD (SEQ ID NO: 89) | QGALYLFGD (SEQ ID NO: 90) |
| VTVYV (SEQ ID NO: 91) | TSVTVYVNN (SEQ ID NO: 92) | TSVTVWVNN (SEQ ID NO: 94) |
|  | QSVTVYVNT (SEQ ID NO: 93) | QSVSVYVNT (SEQ ID NO: 95) |

TNF-α plays a central role in the immune response to infection and inflammation. It is a cytokine that mediates host-resistance against microorganisms, especially intracellular microbes but also is believed to play a key role in autoimmune diseases such as rheumatoid arthritis (RA). Therapies using anti-TNF-α antibodies (e.g., Infliximab brand manes Remicade or Centocor) have been approved for the treatment of RA. (See Haerter, G. et al., Clin Infect Dis. (2004) 39 (9):e88-e94.)

In some embodiments, the invention comprises a method of detecting TNF-α or measuring levels of TNF-α in a human sample using one or more TNF-α-binding peptides disclosed herein. In variations of this embodiment, the patient is suffering from an infection or an autoimmune disease or condition. In some embodiments, the invention is a kit for detecting TNF-α or measuring levels of TNF-α in a human sample, the kit comprising one or more thrombin-binding peptides disclosed herein.

In yet another embodiment, the TNF-α-binding peptide disclosed herein is used to bind and inhibit TNF-α in a patient suffering from an infection or an autoimmune disease or condition. In this embodiment, the method comprises further evolving and selecting one or more of the TNF-α-binding peptide disclosed herein for optimal binding to membrane-bound or soluble forms of TNF-α under physiological conditions, and lack of toxicity.

E. Urokinase-Type Plasminogen Activator (uPA)

In some embodiments, the invention is isolated artificial peptides with specific affinity to human Urokinase-type Plasminogen Activator (uPA). In this embodiment, the invention includes peptides consisting of sequences listed in Table 6, column 1. The invention further includes peptides comprising sequences listed in Table 7, column 1, for example, the peptides consisting of sequences listed in Table 7, columns 2 and 3. In addition to the examples listed in Table 7, columns 2 and 3, shorter or longer peptides (e.g., 5, 6, 7, 8, 9, and up to 20 amino acids) comprising sequences listed in Table 7, column 1 are also part of the invention.

TABLE 7 uPA binders

| Sequences selected from 5-mer libraries | Sequences selected from extension libraries | Sequences selected from substitution/deletion libraries |
|---|---|---|
| NAYFS (SEQ ID NO: 96) | YENAYFSGS (SEQ ID NO: 97) | YENAYFSGSG (SEQ ID NO: 98) |
| | NQNAYFSGNG (SEQ ID NO: 212) | QENAYFSGNG (SEQ ID NO: 99) |
| NDKFS (SEQ ID NO: 100) | VQNDKFSGS (SEQ ID NO: 102) | WGVQNDKFSGS (SEQ ID NO: 103) |
| YNDKF (SEQ ID NO: 101) | | VVWNDKFSGN (SEQ ID NO: 104) |
| HETAR (SEQ ID NO: 105) | CGHETARNW (SEQ ID NO: 106) | CAHETARNW (SEQ ID NO: 107) |
| RSEKF (SEQ ID NO: 108) | YVRSEKFTG (SEQ ID NO: 109) | EGYGRSEKFT (SEQ ID NO: 111) |
| | TARSEKFTG (SEQ ID NO: 110) | WGTGRSEKFT (SEQ ID NO: 112) |

The urokinase-type plasminogen activator (uPA) is a serine protease that plays a major role in fibrinolytic processes, where it converts plasminogen to plasmin. It is a key regulator of tissue inflammation and wound-healing processes. See Sugioka, K., et al. (2014) Invest. Ophthalmol. Vis. Sci. 55:5338. In addition to its well-known function in the fibrinolytic system, uPA is increasingly recognized as a critical component of the inflammatory response by regulating leukocyte extravasation to inflamed tissue. These processes are relevant to acute and chronic cardiovascular diseases. See Reichel, C. et al. (2012) Trends in Cardiovascular Med. 22:192. uPA also plays an important role in tumor invasion and progression in a variety of tumor types. See Fuessel, S. et al. *BMC Cancer* 2014, 14:974. The levels of uPA have diagnostic value for various diseases or conditions. The use of highly specific uPA inhibitors is a strategy for the prevention and treatment of tumors and cardiovascular pathologies.

In some embodiments, the invention comprises a method of detecting uPA or measuring levels of uPA in a human sample using one or more uPA-binding peptides disclosed herein. In variations of this embodiment, the patient is suffering from a tumor or a cardiovascular disease or condition. In some embodiments, the invention is a kit for detecting uPA or measuring levels of uPA in a human sample, the kit comprising one or more uPA-binding peptides disclosed herein.

In yet another embodiment, the uPA-binding peptide disclosed herein is used to bind and inhibit uPA and thus the uPA pathway in a patient suffering from a tumor or a cardiovascular disease or condition. In this embodiment, the method comprises further evolving and selecting one or more of the uPA-binding peptide disclosed herein for optimal binding to uPA under physiological conditions, and lack of toxicity.

EXAMPLES

Example 1. Streptavidin Binders

Library Synthesis

To create a library of peptides, an array of 5-mer peptides synthesized with 18 natural amino acids excluding Cys and Met, any repeat of two or more of the same amino acid, as well as any peptide containing HR, RH, HK, KH, RK, KR. HP, and PQ sequences to identify binders to streptavidin other than other the known HPQ- and HPM-like motifs. The arrays were synthesized with Z linkers (Z is synthesized using a 3:1 mixture of Gly and Ser) or J linkers (J is synthesized using an equimolar mixture of all 20 natural amino acids) and bound to 0.3 µg/ml Cy5-labeled streptavidin in 1×TE binding buffer with 1% alkali soluble casein in the presence of 0.05% Tween 20 at 4° C. overnight. Table 8 shows results of streptavidin binding to the 5-mer library synthesized with different linkers.

TABLE 8

Secondary SA binder core motifs selected using 5-mer libraries with different linkers

| Linker type | Top 5-mer sequences excluding HPQ and RPM motifs |
|---|---|
| 3Z | LAEYH (SEQ ID NO: 113) |
| | NYPDW (SEQ ID NO: 114) |
| | DPFGW (SEQ ID NO: 4) |
| | SWDKW (SEQ ID NO: 115) |
| 1Z | LGEYH (SEQ ID NO: 6) |
| | PAWAH (SEQ ID NO: 3) |
| | DPFGW (SEQ ID NO: 4) |
| | FDEWL (SEQ ID NO: 2) |
| No linker | LRFDT (SEQ ID NO: 116) |
| | NAWAH (SEQ ID NO: 117) |
| | WRGWL (SEQ ID NO: 118) |
| 1J | YGPYK (SEQ ID NO: 119) |
| | FYGKY (SEQ ID NO: 120) |

Extension Libraries

Second step of binder optimization strategy includes extension of the core motifs identified with the 5-mer libraries by two amino acids from both N- and C-terminus using all 20 natural amino acids. For the extension, we used same libraries generated with 3Z linker or no linker as shown in Table 8 above. Table 9 shows three top binders identified for each extension library, XXFDEWLXX (SEQ ID NO:121) and XXPAWAHXX (SEQ ID NO:125), with two different linkers.

TABLE 9

Effect of linker on core motif extension in SA binders

| Core motif | Extension library | Linker | Top selected motifs |
|---|---|---|---|
| FDEWL (SEQ ID NO: 2) | XXFDEWLXX (SEQ ID NO: 121) | 3Z | NSFDEWLNQ (SEQ ID NO: 124) |
| | | | NSFDEWLQK (SEQ ID NO: 8) |
| | | | NSFDEWLAN (SEQ ID NO: 9) |
| | | No linker | DSFDEWLAG (SEQ ID NO: 122) |
| | | | NSFDEWLAG (SEQ ID NO: 123) |
| | | | NSFDEWLNQ (SEQ ID NO: 124) |
| PAWAH (SEQ ID NO: 3) | XXPAWAHXX (SEQ ID NO: 125) | 3Z | PAPAWAHGG (SEQ ID NO: 10) |
| | | | RAPAWAHGG (SEQ ID NO: 11) |
| | | No linker | PVPAWAHGG (SEQ ID NO: 126) |
| | | | YGPAWAHGG (SEQ ID NO: 127) |
| | | | FAPAWAHGG (SEQ ID NO: 128) |
| | | | PAPAWAHGG (SEQ ID NO: 10) |

Although some selected sequences were identical for both types of linker, the data shown in Table 9 for extension libraries clearly demonstrate that selection pathway can be influenced by the library context.

Example 2. Prostate-Specific Antigen (PSA) Binders

We optimized sequence of peptide binders to PSA by using data for the 5-mer array library with 5Z linker and extension arrays with 3Z linker described earlier and performing more extensive substitution/deletion experiments. The results are shown in Table 10.

TABLE 10

PSA binders

| Sequences selected from 5-mer libraries | Extension libraries | Sequences selected from extension libraries | Double substitution/deletion libraries | Sequences selected from substitution/deletion libraries |
|---|---|---|---|---|
| FEVYL (SEQ ID NO: 40) | XXFEVYLXX (SEQ ID NO: 129) | NGFEVYLPG (SEQ ID NO: 130) | GNGFEVYLPGG (SEQ ID NO: 131) | G[GN]QFEVYIPGA (SEQ ID NO: 134) |
| | | GQFEVYLPG (SEQ ID NO: 41) | GGQFEVYLPGG (SEQ ID NO: 132) | GTDFEVYFPKI (SEQ ID NO: 135) |
| | | TDFEVYLPK (SEQ ID NO: 42) | GTDFEVYLPKG (SEQ ID NO: 133) | |
| WTVYA (SEQ ID NO: 45) | XXWTVYAXX (SEQ ID NO: 136) | SEWTVYAGN (SEQ ID NO: 46) | GSEWTVYAGNG (SEQ ID NO: 137) | ASEWTVYAGN[GK] (SEQ ID NO: 139) |
| | | GDWTVYAGN (SEQ ID NO: 47) | GGDWTVYAGNG (SEQ ID NO: 138) | AGDWTVYAGLG (SEQ ID NO: 49) |
| | | | | ALDWQVYAGFG (SEQ ID NO: 50) |
| WEVHL (SEQ ID NO: 51) | XXWEVHLXX (SEQ ID NO: 140) | TGWEVHLGK (SEQ ID NO: 52) | GTGWEVHLGKG (SEQ ID NO: 142) | GTGWEVHLGKG (SEQ ID NO: 142) |
| | | GQWEVHLGK (SEQ ID NO: 141) | GGQWEVHLGKG (SEQ ID NO: 143) | |
| RSILY (SEQ ID NO: 54) | XXRSILYXX (SEQ ID NO: 144) | SCRSILYGQ (SEQ ID NO: 55) | GSCRSILYGQG (SEQ ID NO: 147) | QSCRSILYGDG (SEQ ID NO: 150) |
| | | SCRSILYND (SEQ ID NO: 145) | GSCRSILYNDG (SEQ ID NO: 148) | |
| | | SCRSILYGP (SEQ ID NO: 146) | GSCRSILYGPG (SEQ ID NO: 149) | |

Example 3. Thrombin Binders

We used the 5-mer arrays library with 3Z linker, then extension arrays with 3Z linker and substitution/deletion libraries to identify peptide binders to thrombin as shown in Table 11. Maturation experiments are in progress.

TABLE 11

Thrombin binders

| Sequences selected from 5-mer libraries | Extension libraries | Sequences selected from extension libraries | Double substitution/deletion libraries |
|---|---|---|---|
| PINLG (SEQ ID NO: 57) | XXPINLGXX (SEQ ID NO: 151) | WAPINLGQR (SEQ ID NO: 58) | GWAPINLGQRG (SEQ ID NO: 152) |
| | | PAPINLGNR (SEQ ID NO: 59) | GPAPINLGNRG (SEQ ID NO: 153) |
| VPIRL (SEQ ID NO: 60) | XXVPIRLXX (SEQ ID NO: 154) | YAVPIRLGA (SEQ ID NO: 61) | QYAVPIRLGAG (SEQ ID NO: 155) |
| WPINL (SEQ ID NO: 62) | XXWPINLXX (SEQ ID NO: 156) | RYWPINLGK (SEQ ID NO: 63) | GRYWPINLGKG (SEQ ID NO: 157) |
| | | YRWPINLGK (SEQ ID NO: 64) | GYRWPINLGKG (SEQ ID NO: 158) |
| APVRL (SEQ ID NO: 65) | XXAPVRLXX (SEQ ID NO: 159) | KYAPVRLGS (SEQ ID NO: 66) | GKYAPVRLGSG (SEQ ID NO: 160) |
| RQIFL (SEQ ID NO: 67) | XXRQIFLXX (SEQ ID NO: 161) | DGRQIFLQK (SEQ ID NO: 68) | GDGRQIFLQKG (SEQ ID NO: 162) |
| PIRLK (SEQ ID NO: 69) | XXPIRLKXX (SEQ ID NO: 163) | NWPIRLKPA (SEQ ID NO: 70) | GNWPIRLKPAG (SEQ ID NO: 164) |
| | | YAPIRLKPQ (SEQ ID NO: 71) | GYAPIRLKPQG (SEQ ID NO: 165) |
| PVGSR (SEQ ID NO: 72) | XXPVGSRXX (SEQ ID NO: 166) | GWPVGSRQY (SEQ ID NO: 73) | GGWPVGSRQYG (SEQ ID NO: 167) |
| | | YGPVGSRGF (SEQ ID NO: 74) | GYGPVGSRGFG (SEQ ID NO: 168) |
| RDPGR (SEQ ID NO: 75) | XXRDPGRXX (SEQ ID NO: 169) | ENRDPGRSF (SEQ ID NO: 76) | GENRDPGRSFG (SEQ ID NO: 170) |

Example 4. TNFα Binders

We used the 5-mer arrays library with 5Z linker, then extension arrays with 3Z linker and substitution/deletion libraries to identify peptide binders to TNFα as shown in Table 12.

TABLE 12

TNFα binders

| Sequences selected from 5-mer libraries | Extension libraries | Sequences selected from extension libraries | Double substitution/deletion libraries | Sequences selected from substitution/deletion libraries |
|---|---|---|---|---|
| AIAIF (SEQ ID NO: 77) | XXAIAIFXX (SEQ ID NO: 171) | GPAIAIFGG (SEQ ID NO: 78) | GPAIAIFGG (SEQ ID NO: 78) | GPAVAIFGG (SEQ ID NO: 80) |
| | | QAAIAIFGG (SEQ ID NO: 79) | QAAIAIFGG (SEQ ID NO: 79) | E[AST]AVAIFG[GS] (SEQ ID NO: 172) |
| | | | | Q[AQ]AVAIFGD (SEQ ID NO: 173) |

TABLE 12-continued

TNFα binders

| Sequences selected from 5-mer libraries | Sequences selected from Extension libraries | Sequences selected from extension libraries | Double substitution/deletion libraries | Sequences selected from substitution/deletion libraries |
|---|---|---|---|---|
| TAVFV (SEQ ID NO: 83) | XXTAVFVXX (SEQ ID NO: 174) | GGTAVFVNT (SEQ ID NO: 84) | GGTAVFVNT (SEQ ID NO: 84) | [GQ]GTAVFVVNT (SEQ ID NO: 175) |
| | | SSTAVFVNQ (SEQ ID NO: 85) | SSTAVFVNQ (SEQ ID NO: 85) | DSTAVFVNT (SEQ ID NO: 87) |
| ALYLF (SEQ ID NO: 88) | XXALYLFXX (SEQ ID NO: 176) | NGALYLFGD (SEQ ID NO: 89) | NGALYLFGD (SEQ ID NO: 89) | QGALYLFGD (SEQ ID NO: 90) |
| | | DGALYLFGN (SEQ ID NO: 177) | DGALYLFGN (SEQ ID NO: 177) | |
| VTVYV (SEQ ID NO: 91) | XXVTVYVXX (SEQ ID NO: 178) | TSVTVYVNN (SEQ ID NO: 92) | TSVTVYVNN (SEQ ID NO: 92) | TSV[TS]VWVNN (SEQ ID NO: 179) |
| | | QSVTVYVNT (SEQ ID NO: 93) | QSVTVYVNT (SEQ ID NO: 93) | QSVSNYVNT (SEQ ID NO: 95) |

Example 5. Taq Polymerase Binders

We used the 5-mer arrays library with 5Z linker, then extension arrays with 3Z linker and substitution/deletion libraries to identify peptide binders to TaqPol as shown in Table 13.

TABLE 13

TaqPot binders

| Sequences selected from 5-mer libraries | Sequences selected from Extension libraries | Sequences selected from extension libraries | Double substitution/deletion libraries | Sequences selected from substitution/deletion libraries |
|---|---|---|---|---|
| HEFSF (SEQ ID NO: 14) | XXHEFSFXX (SEQ ID NO: 180) | GQQHEFSFAQ (SEQ ID NO: 15) | GQQHEFSFAQG (SEQ ID NO: 182) | FQQHEF[ST]FAQ[QP] (SEQ ID NO: 185) |
| | | GQHEFSFGT (SEQ ID NO: 16) | GQHEFSFGTGG (SEQ ID NO: 183) | GQHEFSFGPAI (SEQ ID NO: 18) |
| | | YEHEFSFGT (SEQ ID NO: 181) | GYEHEFSFGTG (SEQ ID NO: 184) | |
| HYFEF (SEQ ID NO: 19) | XXHYFEFXX (SEQ ID NO: 186) | GEHYFEFQQ (SEQ ID NO: 20) | GGEHYFEFQQG (SEQ ID NO: 187) | QGEHYF[TS]F[QA]QP (SEQ ID NO: 190) |
| | | GEHYFEFAP (SEQ ID NO: 21) | GEHYFEFAPGG (SEQ ID NO: 188) | GEHYF[TS]FEPAG (SEQ ID NO: 191) |
| | | QQHYFEFEK (SEQ ID NO: 22) | GQQHYFEFEKG (SEQ ID NO: 189) | [AG][QG][GQ]HYFEFEK[QA] (SEQ ID NO: 192) |
| WKAEK (SEQ ID NO: 26) | XXWKAEKXX (SEQ ID NO: 193) | FGWKAEKFN (SEQ ID NO: 27) | GFGWKAEKFNG (SEQ ID NO: 194) | G[FWY]GWKT[ED]KFNS (SEQ ID NO: 195) |
| WDWDW (SEQ ID NO: 29) | XXWDWDWXX (SEQ ID NO: 196) | RSWDWDWKK (SEQ ID NO: 30) | GRSWDWDWKKG (SEQ ID NO: 198) | GRSW[DE]W[DE]WKKT (SEQ ID NO: 200) |
| | | KKWDWDWKW (SEQ ID NO: 197) | GKKWDWDWKWG (SEQ ID NO: 199) | YQLFDW[DE]WKKT (SEQ ID NO: 201) |
| WKEDW (SEQ ID NO: 32) | XXWKEDWXX (SEQ ID NO: 202) | YKWKEDWKW (SEQ ID NO: 33) | GYKWKEDWKWG (SEQ ID NO: 203) | FGKWK[ED][DE]NKWG (SEQ ID NO: 204) |

TABLE 13-continued

TagPot binders

| Sequences selected from 5-mer libraries | Extension libraries | Sequences selected from extension libraries | Double substitution/deletion libraries | Sequences selected from substitution/deletion libraries |
|---|---|---|---|---|
| WTKVK (SEQ ID NO: 35) | XXWTKVKXX (SEQ ID NO: 205) | YEWTKVKNY (SEQ ID NO: 36) | GYEWTKVKNYG (SEQ ID NO: 206) | GYEWTKYKNYG (SEQ ID NO: 208) |
| | | YSWTKVKDY (SEQ ID NO: 37) | GYSWTKVKDYG (SEQ ID NO: 207) | GYSWNKYK[DE]YG (SEQ ID NO: 209) |

Example 6. Urokinase-Like Plasminogen Activator (uPA) Binders

We used the 5-mer arrays library with 5Z linker, then extension arrays with 3Z linker and substitution/deletion libraries to identify peptide binders to uPA as shown in Table 14.

TABLE 14 uPA binders

| Sequences selected from 5-mer libraries | Extension libraries | Sequences selected from extension libraries | Double substitution/deletion libraries | Sequences selected from substitution/deletion libraries |
|---|---|---|---|---|
| NAYFS (SEQ ID NO: 96) | XXNAYFSXX (SEQ ID NO: 210) | YENAYFSGS (SEQ ID NO: 97) | GYENAYFSGSG (SEQ ID NO: 213) | [GT]Y[ED]NAYFSG[SN][GN] (SEQ ID NO: 216) |
| | | FDNAYFSGN (SEQ ID NO: 211) | GFDNAYFSGNG (SEQ ID NO: 214) | TQ[ED]NAYFSGNG (SEQ ID NO: 217) |
| | | NQNAYFSGNG (SEQ ID NO: 212) | GNQNAYFSGNG (SEQ ID NO: 215) | |
| NDKFS (SEQ ID NO: 100) | XXNDKFSXX (SEQ ID NO: 218) | VQNDKFSGS (SEQ ID NO: 102) | GGVQNDKFSGS (SEQ ID NO: 219) | WGVQNDKFSGS (SEQ ID NO: 103) |
| | | | | GVV[WY]NDKFSGN (SEQ ID NO: 220) |
| HETAR (SEQ ID NO: 105) | XXHETARXX (SEQ ID NO: 221) | CAHETARWA (SEQ ID NO: 222) | GCAHETARWAG (SEQ ID NO: 223) | GC[AG]HETARN[WY]G (SEQ ID NO: 225) |
| | | CGHETARNW (SEQ ID NO: 106) | GCGHETARNWG (SEQ ID NO: 224) | |
| RSEKF (SEQ ID NO: 108) | XXRSEKFXX (SEQ ID NO: 226) | YVRSEKFTG (SEQ ID NO: 109) | GGYVRSEKFTG (SEQ ID NO: 227) | EGY[GAQ]RS[ED]KFTG (SEQ ID NO: 229) |
| | | TARSEKFTG (SEQ ID NO: 110) | GGTARSEKFTG (SEQ ID NO: 228) | WG[TS][GAQ]RS[ED]KFTG (SEQ ID NO: 230) |

We have also investigated an effect of linkers on binder selection with 5-mer library. We found that using "no-linker" 5-mer library instead of 5Z library results in selection of a large group of peptides that share the following patterns: XNDK[FY] (SEQ ID NO:231) and XSEKFX (SEQ ID NO:232), where X is any of 20 natural amino acids. NDKFS (SEQ ID NO:100) and RSEKF (SEQ ID NO:108) motifs selected from the 5Z 5-mer library belong to the same two groups. However NAYFS (SEQ ID NO:96) and HETAR (SEQ ID NO:105) motifs would not be detected in the "no-linker" library because of low signal.

Example 7. Characterization of Selected Streptavidin Binders

A selection of streptavidin peptide binders listed in Table 15 were synthesized using standard column-based synthesis techniques by UW Biotechnology center (Madison, Wis.) or by Peptide2.0 (Chantilly, Va.) at 98-99% purity. Strep-tag II peptide NH2-SAWSHPQFEK-COOH was purchased from IBA GmbH (Goettingen, Germany). Notably, peptides were prepared with either a C-terminal amide or carboxylic acid (—COOH) moiety as indicated in Table 15. Synthesized peptides were then characterized by Surface Plasmon Resonance (SPR) to identify binding characteristics including the association rate constant ($k_a$), dissociation rate constant ($k_d$), and equilibrium dissociation rate constant ($k_d/k_a=K_D$). In one aspect, SPR experiments were performed by using Biacore X100 instrument (GE Healthcare). Preliminarily, 60 µl of 100 µg/ml streptavidin in 10 mM Na-acetate, pH5.0 was immobilized to flow cell 2 (Fc2) of a sensor chip CM5 (GE Healthcare) using Amine Coupling Kit (GE Healthcare) at 20° C. for 6 min. Peptide stock solutions were prepared at 5 or 10 mM concentration in water and diluted in HBS-EP+ (GE Healthcare) buffer before SPR experiments. Peptide binding was performed in a multiple kinetics mode using HBS-EP+ as a running buffer and 0.2 M NaCl, 10 mM NaOH or 10 mM HCl-glycine, pH11.7 as regeneration buffer. Binding kinetics parameters were calculated with Biacore X100 software. The resulting data is shown in Table 15.

listed peptide sequence in each grouping (parent peptide) was further matured, extended, or a combination thereof, which generally yielded a peptide binder having a lower equilibrium dissociation constant ($K_D$). In one aspect, the peptide GNSFDDWLASKG (SEQ ID NO:238) exhibited irreversible binding as compared with the parent peptide NSFDDWLAKGG (SEQ ID NO:237). In another aspect, the peptide AFPDYLAEYHGG (SEQ ID NO:241) exhibited the

TABLE 15

Characterized Streptavidin Binders

| Peptide Sequence | KD [uM] | Ka [1/Ms] | Kd [1/s] |
|---|---|---|---|
| NH$_2$-SAWSHPQFEK-COOH (SEQ ID NO: 233) | 49.8 ± 2.4 | | |
| NH$_2$-WTHPQFEQK-COOH (SEQ ID NO: 234) | 15.5 ± 0.23 | | |
| NH$_2$-WTHPQFEQPKA-amide (SEQ ID NO: 235) | 7.9 ± 0.43 | | |
| NH$_2$-EWVHPQFEQKAK-amide (SEQ ID NO: 236) | 5.68 ± 0.29 5.87 ± 0.35 | | |
| NH$_2$-NSFDDWLAKGG-COOH (SEQ ID NO: 237) | 11.3 ± 0.28 | | |
| NH$_2$-GNSFDDWLASKG-amide (SEQ ID NO: 238) | Irreversible Binding | | |
| NH$_2$-ADYLAEYHGG-COOH (SEQ ID NO: 239) | 96 ± 5 | | |
| NH$_2$-AFDYLAQYHGG-amide (SEQ ID NO: 240) | 1.52 | (2.33 ± 0.024) $10^4$ | (3.54 ± 0.015) $10^{-2}$ |
| NH$_2$-AFPDYLAEYHGG-amide (SEQ ID NO: 241) | 0.043 | (3.01 ± 0.11) $10^4$ | (1.28 ± 0.029) $10^{-3}$ |
| NH$_2$-DPAPAWAHGG-COOH (SEQ ID NO: 242) | >500 | | |
| NH$_2$-RDPAPAWAHGGG-amide (SEQ ID NO: 243) | 4.66 | (1.49 ± 0.021) $10^4$ | (6.96 ± 0.026 $10^{-2}$ |

Peptide binders for Streptavidin listed in Table 15 were identified using the methods for peptide binder identification described herein (e.g., core motif discovery, maturation, extension). In one aspect, the peptide SAWSHPQFEK (SEQ ID NO:233) was not identified using the array-based methods for peptide binder identification according to the present disclosure, but is the known Strep-Tag II fusion tag sequence (NOVAGEN) that is capable of binding to an engineered streptavidin protein. The Strep-Tag II peptide (SEQ ID NO:233) was used as a benchmark for comparison with the remaining peptides listed in Table 15. In another aspect, the Strep-Tag II peptide (SEQ ID NO:233) was matured and extended using the methods of the present disclosure to identify the peptides WTHPQFEQK (SEQ ID NO:234), WTHPQFEQPKA (SEQ ID NO:235), and EWVHPQFEQKAK (SEQ ID NO:236), each of which exhibited a decreased $K_D$ as compared with the Strep-Tag II peptide (SEQ ID NO:233).

Three additional groups of peptides listed in Table 15 include: i) NSFDDWLAKGG (SEQ ID NO:237) and GNSFDDWLASKG (SEQ ID NO:238), ii) ADYLAEYHGG (SEQ ID NO:239), AFDYLAQYHGG (SEQ ID NO:240), and AFPDYLAEYHGG (SEQ ID NO:241), and iii) DPAPAWAHGG (SEQ ID NO:242) and RDPAPAWAHGGG (SEQ ID NO:243). For each group, the first lowest $K_D$ of the each of the streptavidin peptide binders in Table 15. In yet another aspect, extension of the peptide DPAPAWAHGG (SEQ ID NO:242) by a single amino acid to the at each of the N-terminus and C-terminus yielded the peptide RDPAPAWAHGGG (SEQ ID NO:243), which resulted in at least a 100-fold change in $K_D$ as compared with the parent peptide.

One or more of the peptides in Table 15 can be used either alone or in combination with another species to form a complex with a molecule of the protein streptavidin, where the complex has a $K_D$ of less than about 10 micromolar (μM). In one aspect, the species associated with the peptide binder can be another peptide or protein, a component having a solid surface such as a bead or a chip, a small molecule, a nucleic acid (e.g., DNA, RNA), the like, and combinations thereof. For example, the peptide binder can be an N-terminal or C-terminal tag added to a protein. In another example, the peptide can be covalently (or otherwise) attached to a magnetic bead. In another aspect, the peptide (either alone or in combination with another species as described above) can form a complex with streptavidin. In one example, the peptide-streptavidin complex has $K_D$ of less than about 100 μM. In another example, the peptide-streptavidin complex has $K_D$ of less than about 10 μM. In yet another example, the peptide-streptavidin complex has $K_D$ of less than about 1 μM. In still another example, the peptide-streptavidin complex has $K_D$ of less than about 0.1 μM As listed in Table 15, the peptide AFPDYLAEYHGG (SEQ ID NO:241) exhibited a measured $K_D$ of 0.043 μM (i.e., less than about 0.1 μM). In another aspect, the peptide RDPAPAWAHGGG (SEQ ID NO:243) exhibited a $K_D$ of about 4.66 μM (i.e., less than about 10 μM). In yet another aspect, the peptide ADYLAEYHGG (SEQ ID NO:239) exhibited a $K_D$ of about 96 μM (i.e., less than about 100 μM).

Additional peptide binders and the associated $K_D$'s for complexes formed with streptavidin are listed in Table 15.

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. An isolated artificial peptide binder bound to a target protein, the isolated artificial peptide binder having specific affinity for the target protein, the artificial peptide binder having at least 5 and up to 20 amino acids, the artificial peptide binder selected from a streptavidin binder comprising a sequence selected from the sequences in Tables 1 and 2; a Taq polymerase binder comprising a sequence selected from the sequences in Table 3; a binder to Prostate Specific Antigen (PSA) comprising a sequence selected from the sequences in Table 4; a thrombin binder comprising a sequence selected from the sequences in Table 5; a binder to Tumor Necrosis Factor comprising a sequence selected from the sequences in Table 6; and a binder to Urokinase-type Plasminogen Activator (uPA) comprising a sequence selected from the sequences in Table 7, wherein the artificial peptide binder is one of an N-terminal tag added to a protein, a C-terminal tag added to a protein, and attached to a solid support through a covalent bond, wherein when the artificial peptide binder is a streptavidin binder, the target protein is streptavidin, wherein when the artificial peptide binder is a Taq polymerase binder, the target protein is Taq polymerase, wherein when the artificial peptide binder is a Prostate Specific Antigen (PSA) binder, the target protein is Prostate Specific Antigen (PSA), wherein when the artificial peptide binder is a thrombin binder, the target protein is thrombin, wherein when the artificial peptide binder is a binder to Tumor Necrosis Factor, the target protein is Tumor Necrosis Factor, and wherein when the artificial peptide binder is a binder to Urokinase-type Plasminogen Activator (uPA), the target protein is Urokinase-type Plasminogen Activator (uPA).

2. The artificial peptide binder to streptavidin of claim 1, comprising a sequence selected from Table 1 (LGEYH (SEQ ID NO:1), FDEWL (SEQ ID NO:2), PAWAH (SEQ ID NO:3), DPFGW (SEQ ID NO:4), and RPGWK (SEQ ID NO:5)).

3. The peptide binder of claim 2, consisting of a sequence selected from Table 2 (DYLGEYHGG (SEQ ID NO:6), NSFDEWLNQ (SEQ ID NO:7), NSFDEWLQK (SEQ ID NO:8), NSFDEWLAN (SEQ ID NO:9), PAPAWAHGG (SEQ ID NO:10), RAPAWAHGG (SEQ ID NO:11), SGDPFGWST (SEQ ID NO:12), RPGWKLW (SEQ ID NO:13)).

4. The artificial peptide binder to Taq polymerase of claim 1, comprising a sequence selected from Table 3 (HEFSF (SEQ ID NO:14), HYFEF (SEQ ID NO:19), WKAEK (SEQ ID NO:26), WDWDW (SEQ ID NO:29), WKEDW (SEQ ID NO:32), WTKVK (SEQ ID NO:35)).

5. The peptide binder of claim 4, consisting of a sequence selected from Table 3 (FQQHEFSFAQQ (SEQ ID NO:17), GQHEFSFGPAI (SEQ ID NO:18), AQGHYFEFEKQ (SEQ ID NO:23), QGEHYFTFQQP (SEQ ID NO:24), GEHYFTFEPAG (SEQ ID NO:25), FGWKTEKFNS (SEQ ID NO:28), RSWDWDWKKT (SEQ ID NO:31), FGK-WKEDNKW (SEQ ID NO:34), YEWTKYKNY (SEQ ID NO:38), YSWNKYKDY (SEQ ID NO:39)).

6. The artificial peptide binder to Prostate Specific Antigen (PSA) of claim 1, comprising a sequence from Table 4 (FEVYL (SEQ ID NO:40), WTVYA (SEQ ID NO:45), WEVHL (SEQ ID NO:51), RSILY (SEQ ID NO:54)).

7. The peptide binder of claim 6, consisting of a sequence selected from Table 4 (GQFEVYIPGA (SEQ ID NO:43), TDFEVYFPKT (SEQ ID NO:44), ASEWTVYAGN (SEQ ID NO:48), AGDWTVYAGLG (SEQ ID NO:49), ALDWQVYAGFG (SEQ ID NO:50), GTGWEVHLGK (SEQ ID NO:53), QSCRSILYGD (SEQ ID NO:56)).

8. The artificial peptide binder to thrombin of claim 1, comprising a sequence selected from Table 5 (PINLG (SEQ ID NO:57), VPIRL (SEQ ID NO:60), WPINL (SEQ ID NO:62), APVRL (SEQ ID NO:65), RQIFL (SEQ ID NO:67), PIRLK (SEQ ID NO:69), PVGSR (SEQ ID NO:72), RDPGR (SEQ ID NO:75)).

9. The peptide binder of claim 8, consisting of a sequence selected from Table 5 (WAPINLGQR (SEQ ID NO:58), PAPINLGNR (SEQ ID NO:59), YAVPIRLGA (SEQ ID NO:61), RYWPINLGK (SEQ ID NO:63), YRWPINLGK (SEQ ID NO:64), KYAPVRLGS (SEQ ID NO:66), DGRQIFLQK (SEQ ID NO:68), NWPIRLKPA (SEQ ID NO:70), YAPIRLKPQ (SEQ ID NO:71), GWPVGSRQY (SEQ ID NO:73), YGPVGSRGF (SEQ ID NO:74), ENRDPGRSF (SEQ ID NO:76)).

10. The artificial peptide binder to Tumor Necrosis Factor alpha (TNFα) of claim 1, comprising a sequence selected from Table 6 (AIAIF (SEQ ID NO:77), TAVFV (SEQ ID NO:83), ALYLF (SEQ ID NO:88), VTVYV (SEQ ID NO:91)).

11. The peptide binder of claim 10, consisting of a sequence selected from Table 6 (GPAVAIFGG (SEQ ID NO:80), EAAVAIFGG (SEQ ID NO:81), QAAVAIFGD (SEQ ID NO:82), GGTAVFVVNT (SEQ ID NO:86), DSTAVFVNT (SEQ ID NO:87), QGALYLFGD (SEQ ID NO:90), TSVTVWVNN (SEQ ID NO:94), QSVSVYVNT (SEQ ID NO:95)).

12. The artificial peptide binder to Urokinase-type Plasminogen Activator (uPA) of claim 1, comprising a sequence selected from Table 7 (NAYFS (SEQ ID NO:96), NDKFS (SEQ ID NO:100), YNDKF (SEQ ID NO:101), HETAR (SEQ ID NO:105), RSEKF (SEQ ID NO:108)).

13. The peptide binder of claim 12, consisting of a sequence selected from Table 7 (YENAYFSGSG (SEQ ID NO:98), QENAYFSGNG (SEQ ID NO:99), WGVQNDKFSGS (SEQ ID NO: 103), VVWNDKFSGN (SEQ ID NO: 104), CAHETARNW (SEQ ID NO: 107), EGYGRSEKFT (SEQ ID NO: 111), WGTGRSEKFT (SEQ ID NO: 112)).

14. The artificial peptide binder to streptavidin of claim 1, wherein a complex of the artificial peptide binder with streptavidin has a $K_D$ of less than about 100 μM.

15. The artificial peptide binder to streptavidin of claim 1, wherein the solid support is one of a bead and a chip.

16. The artificial peptide binder to streptavidin of claim 1, wherein the solid support is a microarray, wherein the artificial peptide binder is immobilized at a specific location on the microarray, and wherein the sequences of peptides at specific locations on the array are known.

17. An isolated artificial peptide binder bound to streptavidin, the isolated artificial peptide binder having specific affinity for streptavidin, the artificial peptide binder having at least 5 and up to 20 amino acids, the artificial peptide binder comprising a sequence selected from LGEYH (SEQ ID NO:1), FDEWL (SEQ ID NO:2), PAWAH (SEQ ID NO:3), DPFGW (SEQ ID NO:4), and RPGWK (SEQ ID NO:5), wherein the artificial peptide binder is one of an N-terminal tag added to a protein, a C-terminal tag added to a protein, and attached to a solid support through a covalent bond.

18. The artificial peptide binder to streptavidin of claim 17, wherein the solid support is one of a bead and a chip.

19. The artificial peptide binder to streptavidin of claim 17, wherein the solid support is a microarray, wherein the artificial peptide binder is immobilized at a specific location on the microarray, and wherein the sequences of peptides at specific locations on the array are known.

20. An isolated artificial peptide binder bound to streptavidin, the isolated artificial peptide binder having specific affinity for streptavidin, the artificial peptide binder having at least 5 and up to 20 amino acids, the artificial peptide binder comprising the sequence AFPDYLAEYHGG (SEQ ID NO:241), wherein the artificial peptide binder is one of an N-terminal tag added to a protein, a C-terminal tag added to a protein, and attached to a solid support through a covalent bond.

* * * * *